United States Patent
Whitman et al.

(10) Patent No.: US 10,813,665 B1
(45) Date of Patent: Oct. 27, 2020

(54) CUTTING DEVICE AND RELATED SYSTEMS AND METHODS

(71) Applicant: GWBN, LLC, Arnold, MD (US)

(72) Inventors: Glenn Whitman, Baltimore, MD (US); William Niland, Arnold, MD (US)

(73) Assignee: GWBN, LLC, Arnold, MD (US)

( * ) Notice: Subject to any disclaimer, the term of this patent is extended or adjusted under 35 U.S.C. 154(b) by 0 days.

(21) Appl. No.: 16/861,735

(22) Filed: Apr. 29, 2020

Related U.S. Application Data

(63) Continuation-in-part of application No. 16/834,068, filed on Mar. 30, 2020, which is a continuation of application No. 16/402,921, filed on May 3, 2019, now Pat. No. 10,603,071.

(51) Int. Cl.
| | | |
|---|---|---|
| *A61B 17/3209* | (2006.01) | |
| *A61B 17/3211* | (2006.01) | |
| *A61B 17/34* | (2006.01) | |
| *A61B 17/00* | (2006.01) | |

(52) U.S. Cl.
CPC .... *A61B 17/3211* (2013.01); *A61B 17/32093* (2013.01); *A61B 17/3417* (2013.01); *A61B 2017/00477* (2013.01); *A61B 2017/32113* (2013.01); *A61B 2017/3454* (2013.01)

(58) Field of Classification Search
CPC .......... A61B 17/3209; A61B 17/32093; A61B 17/3211; A61B 17/3415; A61B 17/3417; A61B 2017/00477; A61B 2017/32113; A61B 2017/3454; A61B 2017/320052; A61M 25/06
See application file for complete search history.

(56) References Cited

U.S. PATENT DOCUMENTS

| | | | |
|---|---|---|---|
| 3,192,624 A | * | 7/1965 | Gringer .................. B26B 5/001 30/162 |
| 4,552,146 A | | 11/1985 | Jensen et al. |
| 4,759,363 A | | 7/1988 | Jensen |
| 4,862,891 A | * | 9/1989 | Smith ................ A61B 17/3417 606/191 |
| 4,955,890 A | | 9/1990 | Yamamoto et al. |
| 5,843,108 A | | 12/1998 | Samuels |
| 6,716,228 B2 | | 4/2004 | Tal |
| 8,512,363 B2 | | 8/2013 | Heppler |
| 9,265,497 B2 | | 2/2016 | Teichman et al. |

(Continued)

FOREIGN PATENT DOCUMENTS

FR   3 017 286   8/2015

OTHER PUBLICATIONS

International Search Report and Written Opinion of the International Searching Authority for International Application No. PCT/US2020/031047 dated Aug. 10, 2020, 13 pages.

*Primary Examiner* — Kathleen S Holwerda
(74) *Attorney, Agent, or Firm* — Cooley LLP

(57) ABSTRACT

Systems, apparatus, and methods are described for forming an incision in tissue for receiving a surgical instrument. A cutting device for forming the incision can be reversibly coupleable to an instrument, e.g., a dilator. The instrument may define a lumen configured to receive a wire that extends or is otherwise extendable through a puncture site. The cutting device can include a cutting element configured to be actuated to form the incision such that the incision extends form the puncture site and is sized to receive the instrument.

30 Claims, 24 Drawing Sheets

(56) References Cited

U.S. PATENT DOCUMENTS

| | | |
|---|---|---|
| 9,480,498 B1 | 11/2016 | Kessler |
| 9,743,950 B2 | 8/2017 | Rauchwerger |
| 10,603,071 B1 * | 3/2020 | Whitman .............. A61M 25/06 |
| 2002/0099402 A1 | 7/2002 | Buckman et al. |
| 2004/0181246 A1 | 9/2004 | Heppler |
| 2005/0177183 A1 | 8/2005 | Thorne et al. |
| 2007/0027463 A1 | 2/2007 | Neubig |
| 2009/0143808 A1 | 6/2009 | Houser |
| 2012/0226299 A1 * | 9/2012 | Heppler ............. A61B 17/3211 |
| | | 606/167 |
| 2013/0197558 A1 * | 8/2013 | Ingold, Jr. ........ A61B 17/32093 |
| | | 606/185 |
| 2013/0218183 A1 | 8/2013 | Rauchwerger |
| 2014/0142605 A1 | 5/2014 | Lopera |
| 2015/0289901 A1 | 10/2015 | Khan et al. |
| 2016/0128713 A1 | 5/2016 | Rauchwerger et al. |

\* cited by examiner

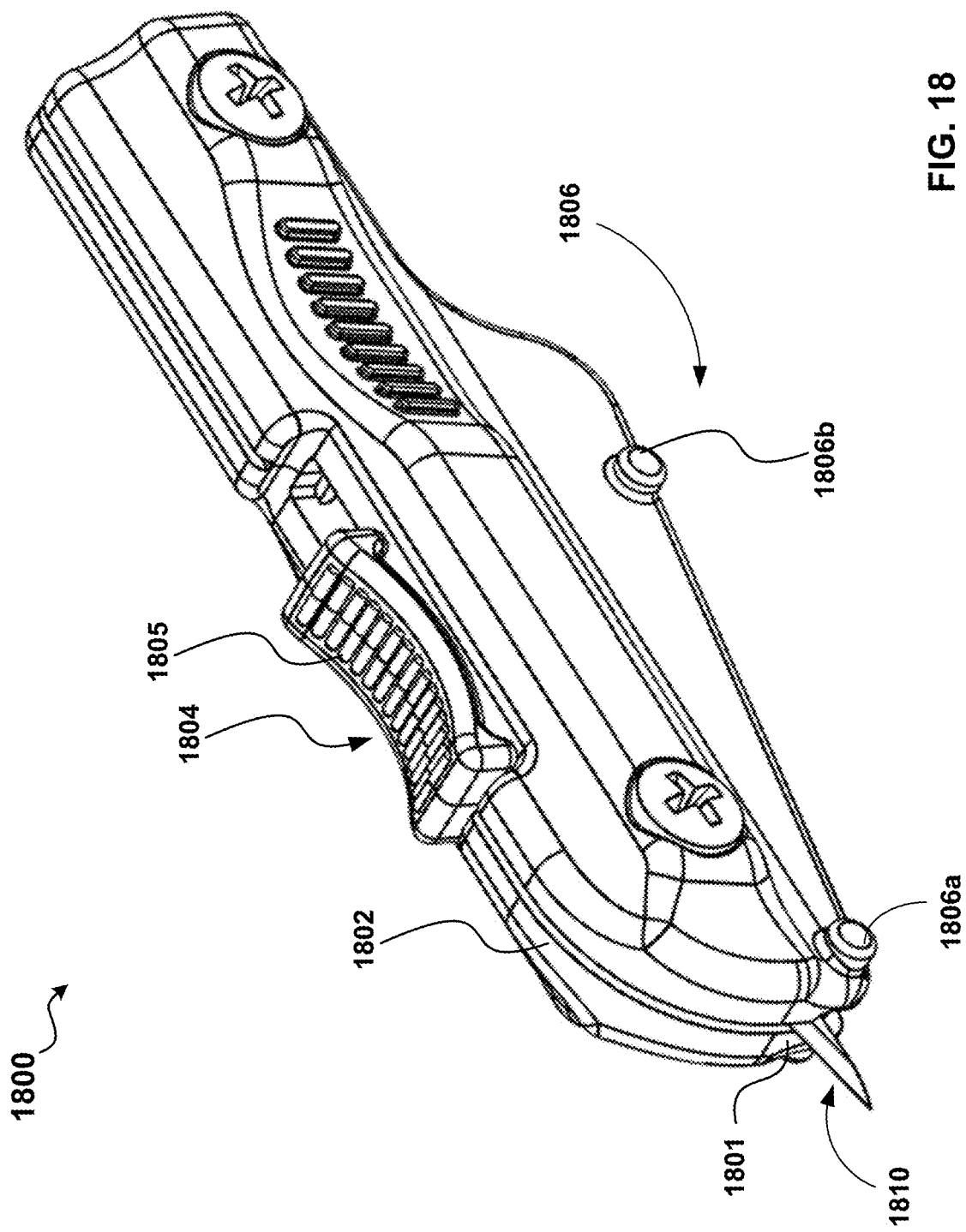

CUTTING DEVICE AND RELATED SYSTEMS AND METHODS

CROSS-REFERENCE TO RELATED APPLICATIONS

This application is a continuation-in-part of U.S. patent application Ser. No. 16/834,068, filed Mar. 30, 2020, titled "Cutting Device and Related Systems and Methods," which is a continuation of U.S. patent application Ser. No. 16/402,921, filed May 3, 2020, titled "Cutting Device and Related Systems and Methods," now U.S. Pat. No. 10,603,071, the disclosures of which are incorporated by reference herein.

TECHNICAL FIELD

The present disclosure relates generally to systems, apparatus, and methods for deploying a medical instrument into a body lumen of a subject during a medical procedure, and in particular, to a cutting device capable of forming an incision for receiving a medical instrument, such as a catheter, into a body lumen of a subject.

BACKGROUND

Intravascular medical devices such as catheters are deployed in many medical procedures. Use of intravascular catheters, however, can lead to bloodstream infections, which can be costly to treat and/or result in death or other health complications. For example, an infection can result from skin organisms that migrate from an insertion site of a catheter onto and along an external surface of the catheter. This migration of skin organisms along the catheter which dwell within a central vessel, artery, or vein, can lead to a blood stream infection. In many hospitals in the U.S. including high performing intensive care units, this type of event occurs approximately 1-3 times every 1000 central line days, and sometimes far more. Infections can also be tied to use of other types of catheters placed for other reasons to provide medical care, including catheters such as dialysis catheters, cannulation catheters for extracorporeal membrane oxygenation (ECMO), and chest tubes placed within the pleural cavity.

A catheter or other intravascular medical device can be delivered into blood vessels, organs, body cavities, and other anatomic sites ("target site(s)" or "target anatomical site(s)") using a variety of techniques. One commonly used technique to gain access to a target site (e.g., a blood vessel) is the Seldinger technique. The Seldinger technique involves penetrating through skin tissue overlying a blood vessel of a subject with a sharp hollow object, typically a hollow needle. A wire (e.g., a guidewire) can then be advanced via a lumen of the needle into the blood vessel, and the needle can be withdrawn over the guidewire and removed.

Following placement of the wire but prior to insertion of the catheter or other intravascular device, an incision (e.g., "skin-nick," in cases where the diameter of the catheter is small) in the skin tissue is formed through the skin at or adjacent to the opening formed by the needle (i.e., the entry site for the wire). If formed properly, the incision will start at the opening or puncture site of the needle, and have a length approximately equal to the diameter of the catheter to be subsequently inserted. After the incision is formed, the catheter or other medical instrument can then be passed over the wire, through the incision, and into the blood vessel or body cavity.

While techniques such as the Seldinger technique can be used to deploy a catheter or other medical instrument into a target site, such as a blood vessel, they can be difficult and/or time-consuming to perform properly. For example, complications can occur with the creation of the incision, e.g., where the incision does not initiate at the opening of the puncture site resulting in a skin-bridge, the incision is too large, or the incision is too long. When these complications arise, it may be impossible (or additional measures may be required) to insert the dilator or catheter (or other medical instrument(s)) over the Seldinger wire into the target vessel, such as in the case of a skin bridge). Alternatively, if an incision is too large, bleeding may occur around the catheter, which can be substantial, or the incision itself, being open, can provide a site for colonization, either of which increases the risk of bacterial colonization at the catheter entry site, increasing the risk of a blood stream infection. Accordingly, it is desirable to have systems and methods that reduces the difficulty and/or skill required to gain access to a target site, thereby reducing complications associated with use of any invasive catheter.

SUMMARY

According to an aspect of the present disclosure, an apparatus for forming a controlled incision in tissue is provided. The apparatus may include a coupling mechanism (e.g., a reversible coupling mechanism) configured to couple the apparatus to a dilator having a tapered distal end and a hub at a proximal end. The dilator may define a lumen configured to receive a wire that extends or is otherwise extendable through a puncture site. The apparatus may further include a proximal end configured to abut the hub of the dilator when the apparatus is coupled to the dilator. The apparatus may further include a cutting element including an inner edge and an outer cutting edge. The cutting element may be configured to be movable between a retracted position and an extended position, in which the inner edge extends along the tapered distal end of the dilator. The outer cutting edge may be configured to form an incision extending from the puncture site, thereby preventing the formation of a skin bridge. Furthermore, the cutting element can be configured to form an incision that has a length that is equal to a diameter of a catheter (or other medical instrument) that is inserted into the incision.

According to an aspect of the present disclosure, a method for deploying a catheter or other medical instrument into a body lumen is provided. The method may include advancing a dilator, over a wire positioned through a puncture site formed in a tissue, toward the puncture site. The dilator may have a reversibly attached cutting device including a cutting element configured to cut the tissue. The method may further include moving the cutting element from a retracted position to an extended position. The method may further include inserting the distal end of the dilator and the cutting element into the tissue such that the cutting element forms an incision extending from the puncture site and sized to receive a surgical instrument.

According to an aspect of the present disclosure, a kit including a system for deploying a medical instrument is provided. The kit may include a dilator defining a lumen configured to receive a wire that extends or is otherwise extendable through a puncture site. The dilator may include a hub at a proximal end and a tapered distal end. The kit may further include a cutting device including a cutting element configured to form an incision extending from the puncture site. The cutting element may be configured to be movable between a retracted position and an extended position. The cutting device may be configured to be reversibly coupled to the dilator such that a portion of the cutting element extends to the distal end of the dilator when the cutting element is in the extended position.

It should be appreciated that all combinations of the foregoing concepts and additional concepts discussed in greater detail below (provided such concepts are not mutually inconsistent or exclusive) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present disclosure, and be protected by the accompanying claims.

BRIEF DESCRIPTION OF THE DRAWINGS

The drawings are not necessarily to scale. The drawings are merely schematic representations, not intended to portray specific parameters of the invention. The drawings are intended to depict only typical embodiments of disclosed systems, apparatus, and methods. In the drawings, like reference characters refer to like elements (e.g., functionally similar and/or structurally similar elements).

FIG. 18 depicts a perspective view of a cutting device, according to embodiments.

FIG. 21 depicts a cutting element of the cutting device in a first, extended configuration, and FIG. 2 depicts the cutting element in a second, retracted configuration.

DETAILED DESCRIPTION

Figure 1:
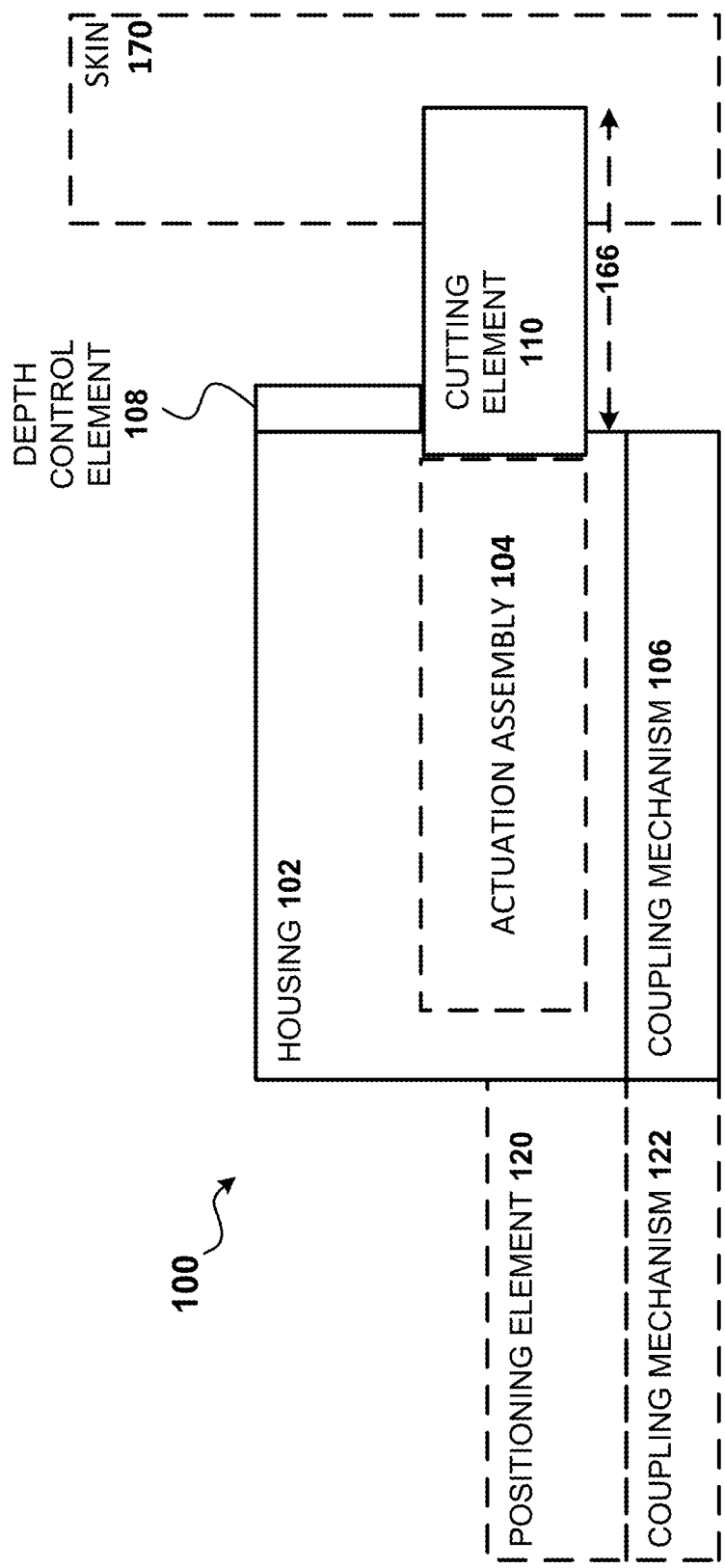
FIG. 1 is a schematic diagram depicting a cutting device, according to an embodiment.

Embodiments of the present disclosure are directed to systems, apparatus, and methods for providing access to a target site (e.g., a blood vessel) such that a medical instrument, e.g., a catheter, can be deployed in the target site. Specifically, systems, apparatus, and methods described herein can be used to form an incision in tissue of a subject during a vascular access procedure and/or other procedures involving placement of a medical device into a body cavity.

Vascular access procedures, such as, for example, the Seldinger technique, can be used to provide access to a target body lumen (e.g., vessel, pleural space) by deploying a medical instrument (e.g., a catheter) into the target body lumen. For example, when the Seldinger technique is used, a target body lumen (e.g., vessel, pleural space) may be accessed percutaneously by puncturing skin of the subject with a hollow needle, inserting a guidewire through the hollow needle so as to position the distal end of the guidewire in the target body lumen. The needle can be withdrawn, leaving the wire in place. To accommodate a placement of a catheter or other medical instrument, the diameter of the skin puncture site traversed by the wire can be enlarged or dilated. To accomplish this, the operator can create a skin incision extending from the puncture site and having a length equal to the diameter of the catheter or other medical instrument. Once that incision is formed, a dilator (or one or more increasingly larger dilators) is passed over the Seldinger wire, creating a track (e.g., opening) suitable to accommodate the final catheter or medical instrument to be inserted into the target body lumen.

The incision can be formed using a cutting device, such as, for example, a blade or scalpel, to form the incision. The physician can hold the guidewire using one hand, and the cutting device using his or her other hand, and then via visual guidance, create the incision, which can receive the dilator, catheter, and/or other medical instrument. If properly performed (e.g., if the incision is properly created or formed), the incision extends from the puncture site and has a length equal to but not longer than the diameter of the catheter or other instrument to be inserted through the incision. Complications, however, can arise when the incision is not properly formed. For example, when the incision is too long, it allows leakage of bodily fluids around the catheter when it is positioned, compromising the ability of the skin to function as a barrier to infection. For example, an incision too long compromises the ability of the skin to form a biological seal around the catheter, which would normally prevent migration of bacteria or other disease-causing agents into the target body lumen. Furthermore, an oversized incision allows blood to leak out around the catheter skin entry site, which can be substantial, particularly in situations where a subject has received an anticoagulant. In these cases, the incision may require stitches to better approximate the skin against the catheter so as to prevent bleeding.

Figure 17A:
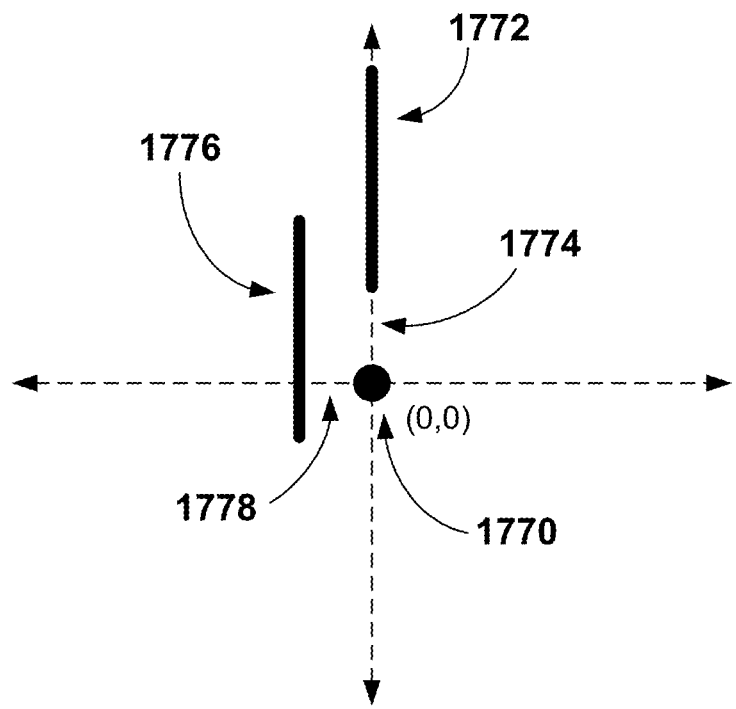
FIGS. 17A and 17B schematically depict a puncture site and incision along a skin surface.
Figure 17B:
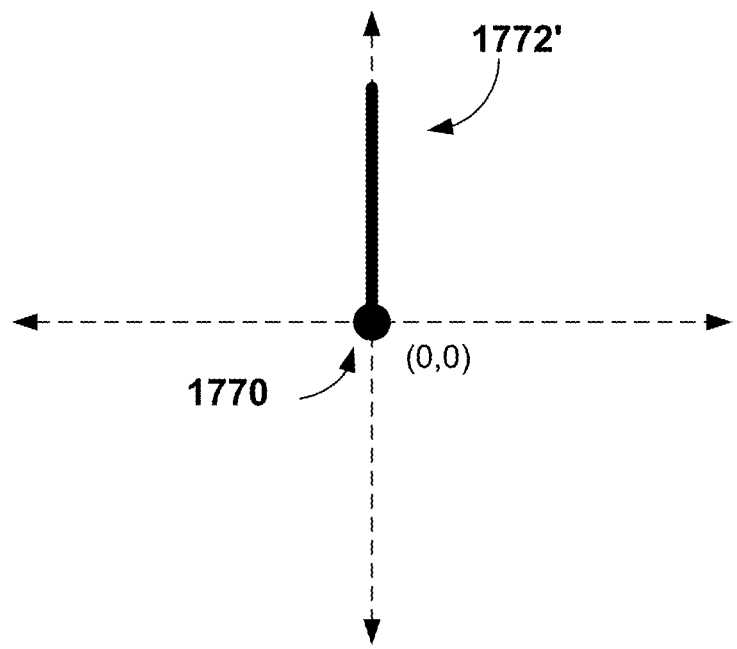
Figure 19:
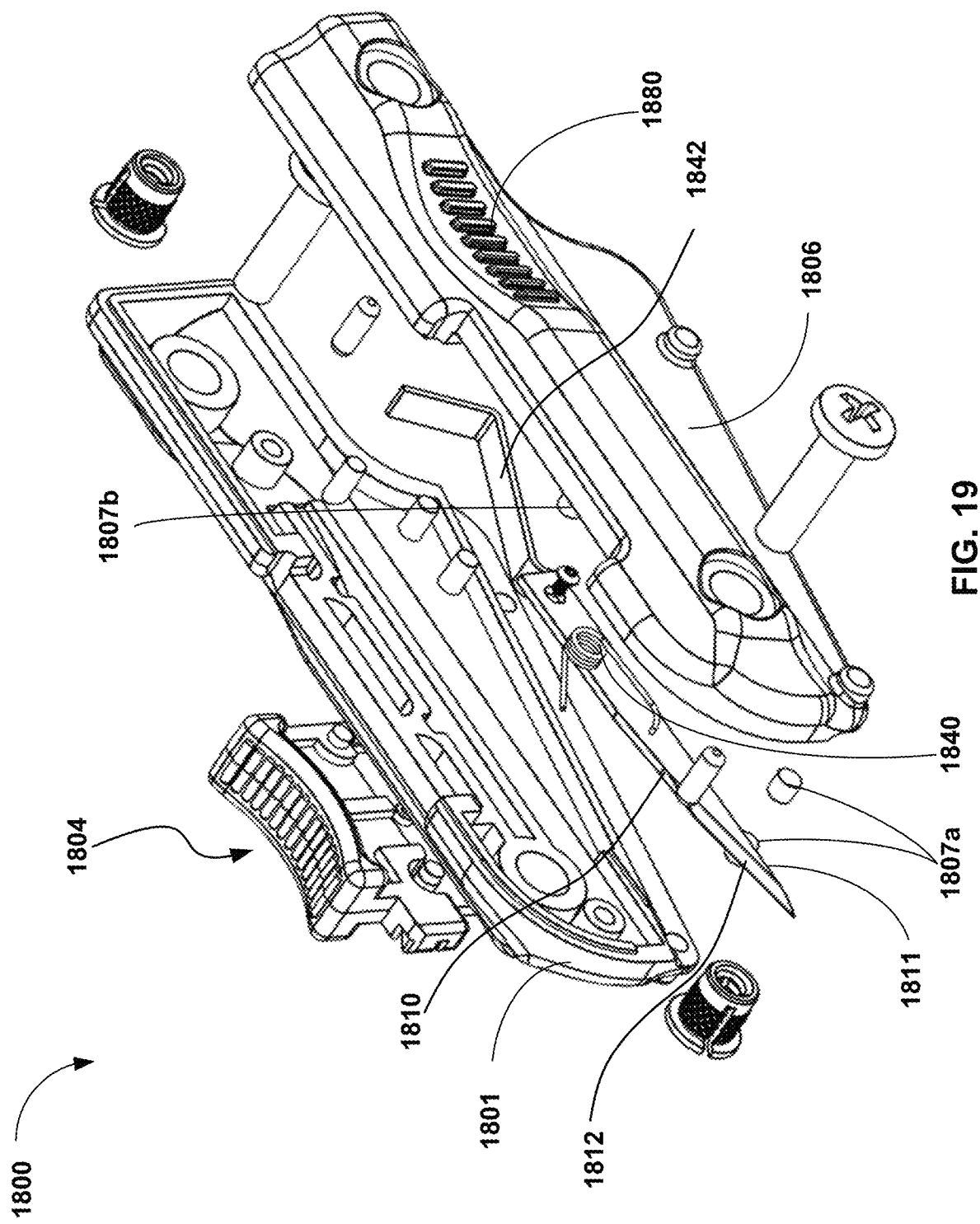
FIG. 19 depicts an exploded view of the cutting device shown in FIG. 18, according to embodiments.

As another example, if the incision does not involve the entry site made by the needle (i.e., in which the Seldinger wire sits), but leaves a skin bridge between the incision and the initial entry site created by the needle, the ensuing dilator and/or other medical instrument can be prevented from being passed along the wire and through the entry site. FIG. 17A schematically illustrates cases where a skin bridge can form. As depicted, skin bridges 1774, 1778 can form when an incision 1772, 1774 does not overlap with an opening of the puncture site 1770. For example, a skin bridge 1774 can form when an incision 1772 does not initiate at the puncture site 1770, even if that incision is aligned with the puncture site 1770. And a skin bridge 1778 can form when an incision 1776 is offset from the puncture site 1770 (e.g., not aligned with the puncture site 1770). These skin bridges 1774, 1778 can prevent a dilator or other instrument from being inserted into the skin. In practice, a physician may move a guidewire after forming the incision 1772 to determine whether there is a skin bridge 1774, 1778, e.g., by visibly inspecting whether the guidewire appears to be moving along a length of the incision. But with skin having some elasticity and with poor visibility surrounding the puncture site (e.g., caused by blood pooling around the puncture site and incision), it may not be possible to determine whether a skin bridge has formed even if it appears the guidewire is moving along the incision. If a physician fails to identify that there is a skin bridge 1774, 1778 and pushes a dilator or other instrument down along the guidewire (e.g., forces a dilator or other instrument down on the guidewire), the physician can bend or damage the guidewire. Then, even if the physician were to detect the skin bridge 1774, 1778 and cut it away, e.g., with a second incision, the bent guidewire can prevent the dilator or other instrument from being inserted into the skin. The second incision combined with the first incision 1772, 1776 can also lead to an incision size that is not sized to that of the dilator or other instrument, which as detailed above, can lead to migration of bacteria. Therefore, when complications arise with a skin bridge, the physician may have no other option than to remove the guidewire and restart the procedure. Systems, devices, and methods described herein are designed to prevent the formation of a skin bridge, i.e., by ensuring that an incision extends from a puncture site, as depicted in FIG. 17B with incision 1772' extending from puncture site 1770. Further details of such systems, devices, and methods are provided below.

Similarly, if the incisional length is too short, the dilator and/or other medical instrument can be prevented from passing deeper than the level of the skin. In particular, if the incision does not extend from the puncture site, a skin-bridge can result. The skin bridge can prevent the catheter from being properly inserted into the target body lumen (i.e., because the skin bridge separates the puncture site from the incision), leading to bending of the Seldinger wire, and preventing its use as the dilator may not be able to pass over the bent wire, even after the skin bridge has been, by necessity, incised. And if the incision is too long, this can prevent the skin or tissue surrounding the opening from sealing around the catheter or instrument, which can enable disease-causing agents (e.g., microorganisms, bacteria, viruses) to migrate along an external surface of the catheter into the target body lumen.

In the situations described above, if the problem is initially unrecognized, forcing the dilator can bend the wire or damage the dilator and/or other medical instrument, which can require the deployment procedure to be repeated. Repeating the deployment procedure can involve repeated accessing of the vessel or body cavity, with its inherent dangers and patient discomfort, and/or the need of a new wire and/or insertion kit.

Systems, apparatus, and methods described herein can reduce the risk of complications resulting from placement of a catheter or other instrument into a body lumen. As further described below, a cutting device can be designed to consistently form a controlled incision in skin that addresses the aforementioned problems, allowing for placement of the desired catheter or instrument into a body lumen without complications.

As illustrated schematically in FIG. 1, an example cutting device 100 can include a housing 102, a cutting element 110, and a coupling mechanism 106. The example cutting device 100 can be placed proximate to a skin 170 of a subject and used to form an incision in the skin 170, e.g., by moving the cutting element 110 through the skin 170. The housing 102 can support the cutting element 110 and optionally include an actuation assembly or mechanism 104 designed to actuate the cutting element 110 to form the desired incision in the skin 170.

In some embodiments, the housing 102 can define a volume, recess, or area for housing the cutting element 110 in a retracted or undeployed position such that a cutting surface of the cutting element 110 is shielded when the cutting element is not in use. The actuation assembly 104 can be designed to move the cutting element 110 forward, e.g., as schematically depicted using arrow 166, to position the cutting element 110 in an extended or deployed position, such that the cutting element 110 can form an incision in the skin 170. The actuation assembly 104 can include one or more actuation mechanisms for deploying the cutting element 110, i.e., for moving the cutting element 110 from an undeployed position into a deployed position, as well as allowing for differential incision lengths. In some embodiments, the actuation assembly 104 can include mechanical components for deploying the cutting element 110. For example, the actuation mechanism 104 can include a trigger that can be actuated to release a pre-loaded spring or other elastic component that can generate a force to deploy the cutting element 110. In some embodiments, the actuation assembly 104 can include a movable component or actuator (e.g., a slider, button, tab, lever) that can be moved (e.g., slid along a length of the housing 102) to deploy the cutting element 110. In some embodiments, the actuation mechanism 104 can include electrically powered components (e.g., components driven and/or powered by a battery or other power source) for deploying the cutting element 110. In some embodiments, the actuation assembly 104 can include components driven mechanically, electrically, magnetically, pneumatically, hydraulically, etc.

The cutting element 110 can include one or more cutting surfaces or blades that are designed to penetrate through the skin 170 to form an incision. Alternatively or additionally, the cutting element 110 can include other mechanisms, e.g., a drill, an electrode, etc., for cutting through the skin 170. The cutting element 110 can be coupled to (e.g., mounted to) housing 102 in a fixed or movable relation, e.g., allowing for a variable length incision. Furthermore, in some embodiments, the cutting element 110 can be movably coupled to housing 102 such that it can move between an undeployed position and a deployed position, e.g., as represented by arrow 166. In some embodiments, the cutting element 110 can be removably coupled to housing 102. For example, the cutting element 110 can be designed to be removed or detached from housing 102, such that the cutting element 110 can be replaced after a single or limited number of uses. In some embodiments, the cutting element 110 and/or housing 102 can be disposable components that can be disposed of after a single use, e.g., after being used to provide access to a target site in the subject.

The housing 102 can be ergonomically shaped such that a user (e.g., a physician) can hold (e.g., grip) the housing 102 in single hand. Optionally, if the actuation assembly 104 is present, the actuation assembly 104 can be positioned on or about the housing 102 such that the user can actuate the actuation assembly 104 while maintaining his hold (e.g., grip) on the housing 102 with a single hand. For example, the actuation assembly 104 can be a slide that can be moved, e.g., using a thumb of a user, to actuate the cutting element 110 during a medical procedure. The housing 102 and cutting element 110 can be formed from lightweight material such that a user can comfortably hold the housing 102 and cutting element 110 without feeling additional strain during a medical procedure.

The cutting device 100 can include a depth control element 108 that is integrated into and/or coupled to the housing 102 and/or cutting element 110. The depth control element 108 can be designed to limit a depth of penetration or insertion of the cutting element 110 into the skin 170 so as to control a size of the incision formed by the cutting element 110 in the skin 170. In some embodiments, the depth control element 108 can be designed to contact a surface of the skin 170 to control a depth of insertion of the cutting element 110. For example, the depth control element 108 can include a surface, protrusion, or other physical structure that can be disposed at a point along the cutting element 110 and/or housing 102 such that it would contact a surface of the skin 170 when the cutting element 110 has been inserted a predetermined depth into the skin 170. In some embodiments, the depth control element 108 can include one or more components that restrict movement of the cutting element 110, thereby controlling a depth of insertion of the cutting element 110. For example, the depth control element 108 can include one or more protrusions and/or surfaces that interfere (e.g., lock) with one another to prevent further movement of the cutting element 110 in a direction toward the skin 170 after the cutting element 110 has penetrated a predetermined depth into the skin. In some embodiments, the depth control element 108 can include one or more sensor(s) (e.g., a light sensor, a pressure sensor, etc.) that can be designed to sense or detect a depth of insertion.

The coupling mechanism 106 can include one or more components designed to couple the housing 102 (or other components of the cutting device 100) to an instrument (e.g., a dilator, a catheter, etc.). In some embodiments, the coupling mechanism 106 can be designed to reversibly couple the housing 106 to the instrument. For example, the coupling mechanism 106 can be designed to couple and decouple the housing 106 to the instrument and/or additional instruments, as many times as needed without comprising its structure. In some embodiments, the coupling mechanism 106 can include mechanical components, e.g., a clasp, a clip, etc. that can attach around the instrument to couple the housing 102 to the instrument. The mechanical component can be designed to be flexible such that it can bend to fit around (e.g., grip onto) the instrument. Alternatively or additionally, the mechanical component can be designed to be mechanically biased (e.g., with a spring) or electrically driven to change between different configurations for attaching to and/or detaching from the instrument. The coupling mechanism 106 can be configured to maintain the coupling between the housing 102 and the instrument by interference fit, press fit, friction fit, and the like. In some embodiments, the coupling mechanism 106 can be configured to allow coaxial movement of the instrument such that the housing 102 (and other components of the cutting device 100) can slide or move along a length of the instrument. The coupling mechanism 106 can be integrated into or attached to the housing 102. As further described with reference to FIG. 2, the coupling mechanism 106 can be configured to attach the housing 102 (or other components of the cutting device 100) to the instrument such that the cutting element 110 is positioned to create an incision in the skin 170 for receiving the desired instrument. In some embodiments, the coupling mechanism 106 can be sized to a specific size of instrument. Alternatively, the coupling mechanism 106 can be configured to couple to instruments within a range of sizes, e.g., such as with adjustable components (e.g., an adjustable clamp or a deformable plug that accommodates a range of sizes).

In some embodiments, a positioning element 120 can optionally be used with the cutting device 100 to assist with proper positioning of the device along a length of the instrument. For example, the positioning element 120 can be designed to couple (e.g., attach) to the instrument, e.g., via a coupling element (e.g., coupling element 122), and extend along a length of the instrument to indicate the location at which the cutting device 100 should attach to the instrument. When used with the cutting device 100, the positioning element 120 can prevent the cutting device 100 from being attached to the instrument at a position that does not enable the cutting instrument to form a properly sized incision in the tissue 170. In some embodiments, the positioning element 120 can be a spacer configured to extend from a proximal end or portion of the instrument to the location at which the cutting device 100 is designed to attach to the instrument, as further described with reference to FIG. 2.

The coupling mechanism 122 can be structurally and/or functionally similar to the coupling mechanism 106, but is designed to couple the positioning element 120 to the instrument, as represented by line 262. For example, the coupling mechanism 122 can include a mechanical component (e.g., a clip or clasp) that is designed to reversibly couple (e.g., couple and decouple multiple times) the positioning element 120 to the instrument such as by interference fit, press fit, friction fit, and the like. The coupling mechanism 122 can be integrated into or attached to the positioning element 120 so as to enable and facilitate reversible coupling of the positioning element 120 to the instrument, such as described herein. The positioning element 120 and the housing 102 can be separately and individually attachable to and removable from the instrument.

In some embodiments, as an alternative to having a separate positioning element (e.g., positioning element 120), the cutting device 100 can include a component (e.g., a protrusion) that can assist with positioning the cutting device 100 along a length of the instrument. For example, the cutting device 100 can include a beam, rod, or other like structure that can be configured to extend from a proximal end of the housing 102 to a proximal end or portion of the instrument, such that when the cutting device 102 is attached to the instrument (e.g., via the coupling mechanism 106), such structure indicates the location at which the cutting device 100 should be positioned relative to the proximal or distal end of the instrument.

Figure 2:
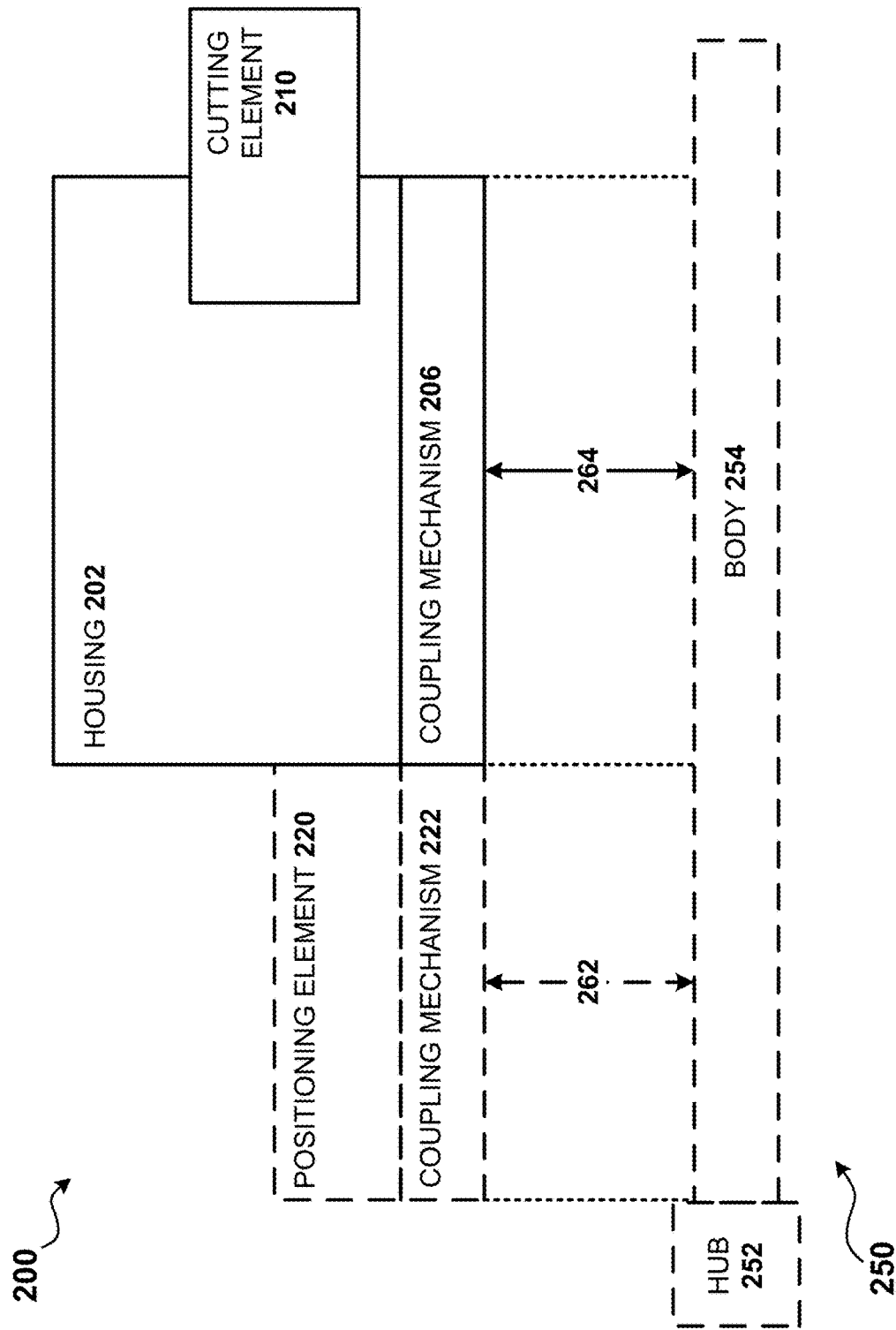
FIG. 2 is a schematic diagram depicting a cutting device and a medical device with which the cutting device can be used, according to an embodiment.

The positioning of a cutting device relative to an instrument can be further understood with reference to FIG. 2. As illustrated schematically in FIG. 2, an example cutting device 200 is shown in relation to an example instrument 250 (e.g., a surgical instrument) with which the cutting device 200 can be used. The cutting device 200 can be structurally and/or functionally similar to the cutting device 100. For example, the cutting device 200 can include a housing 202, a cutting element 210, and a coupling mechanism 206. The instrument 250 can include a hub 252 and a body 254. The cutting device 200 can be reversibly attachable to and/or supportable by the instrument 250, e.g., via the coupling mechanism 206 attaching to the body 245 of the instrument 250, as represented by line 264. The body 254 of the instrument 250 can include portions that are rigid and/or flexible.

In some embodiments, the cutting device 200 can optionally include or be used with a positioning element 220. In some embodiments, positioning element 220 can be a spacer that is configured to define the appropriate spacing between a proximal portion (e.g., hub 252) of the instrument 250 and a proximal end of the housing 202 supporting the cutting element 210. For example, the positioning element 220 can be configured to couple to the body 254 of the instrument 250, e.g., via coupling mechanism 222, such that it extends from the hub 252 of the instrument 250 to a point along a length of the body 254 of the instrument 250 at which the housing 202 is intended to attach to the body 254. When the housing 202 is attached to the body 254 of the instrument 250, a proximal end of the housing 202 can be adjacent to a distal end of the positioning element 220 such that the positioning element 220 extends longitudinally along a length of the body 254 between the hub 252 and the housing 202. The positioning element 220, by extending between the hub 252 and the housing 202, can be configured to prevent proximal movement of the housing 202 relative to the instrument 250. Stated differently, the positioning element 220 can be designed to maintain the housing 202 in a fixed spatial relation with respect to the instrument 250.

The cutting device 200 (and optionally positioning element 220) can be used to form a skin incision in skin (e.g., skin 170) for receiving the instrument 250, e.g., such that the instrument 250 can be received into a target body lumen (e.g., a blood vessel). The instrument 250 can be, for example, a dilator, a catheter, a chest tube, or the like. In an embodiment, the instrument 250 can be a dilator that has a distal end configured to be inserted through the incision and a proximal end including a hub 252. The dilator can have a tapered distal end that facilitates insertion into and subsequent dilation of tissue and/or blood vessels deep to the level of the skin incision (e.g., deeper than a level of the skin incision in skin 170). In some embodiments, the dilator can range in size from about 3 French to about 12 French (i.e., about 1 mm to about 4 mm), including all values and subranges in between. The instrument 250 can include a lumen that extends throughout a length of the instrument 250, i.e., through a length of the hub 252 and a length of the body 254. The lumen can be configured to receive a guidewire, e.g., for steering or guiding the instrument 250 into the target body lumen.

In use, the cutting device 200 can be coupled to the instrument 250 such that the cutting element 210 can be configured to form an incision for receiving the instrument 250, e.g., as part of the Seldinger technique. For example, a needle can be used to create a puncture site in tissue (e.g., tissue 170), and a guidewire can be inserted through the needle into a body lumen (e.g., a blood vessel) deep to the insertion site at the skin level. The needle can be removed, and the instrument 250 (e.g., a dilator) with the housing 202 and optionally the positioning element 220 coupled to its body 254, e.g., via coupling mechanisms 206 and/or 222, can be slid over the guidewire until a distal end of the instrument 250 contacts a surface of the skin. The cutting element 210 can then be actuated to form an incision in the skin that extends from the puncture site and is sized to receive the instrument 250. The housing 202 can be attached to the instrument 250 at a specific location that enables the cutting element 210, when actuated, to form such an incision. The positioning element 250, for example, can be used to set a spacing or distance between a proximal portion (e.g., hub 252) of the instrument 250 and the housing 202, to ensure proper positioning of the housing 202 relative to the instrument 250. Once the incision is formed, the housing 202 and/or positioning element 220 can be removed (e.g., detached, decoupled) from the instrument 250, and the instrument 250 can be inserted through the incision into the body (e.g., and into a lumen or cavity). If the instrument 250 is a dilator (or dilators), the dilator (or dilators) can be used to dilate the tissue and/or blood vessels deep to the incision, and be subsequently withdrawn over the guidewire allowing the appropriately sized catheter (or other instrument) to be guided down the guidewire and placed in the body lumen.

In some embodiments, where the instrument 250 includes a tapered distal end, e.g., such as a dilator with a tapered distal end, the cutting element 210 can be supported such that it is angled toward the puncture site (e.g., angled to follow the taper of the instrument 250), such that the cutting element 210 can form an incision that extends from the puncture site, e.g., preventing any possibility of leaving a skin bridge.

Figure 3:
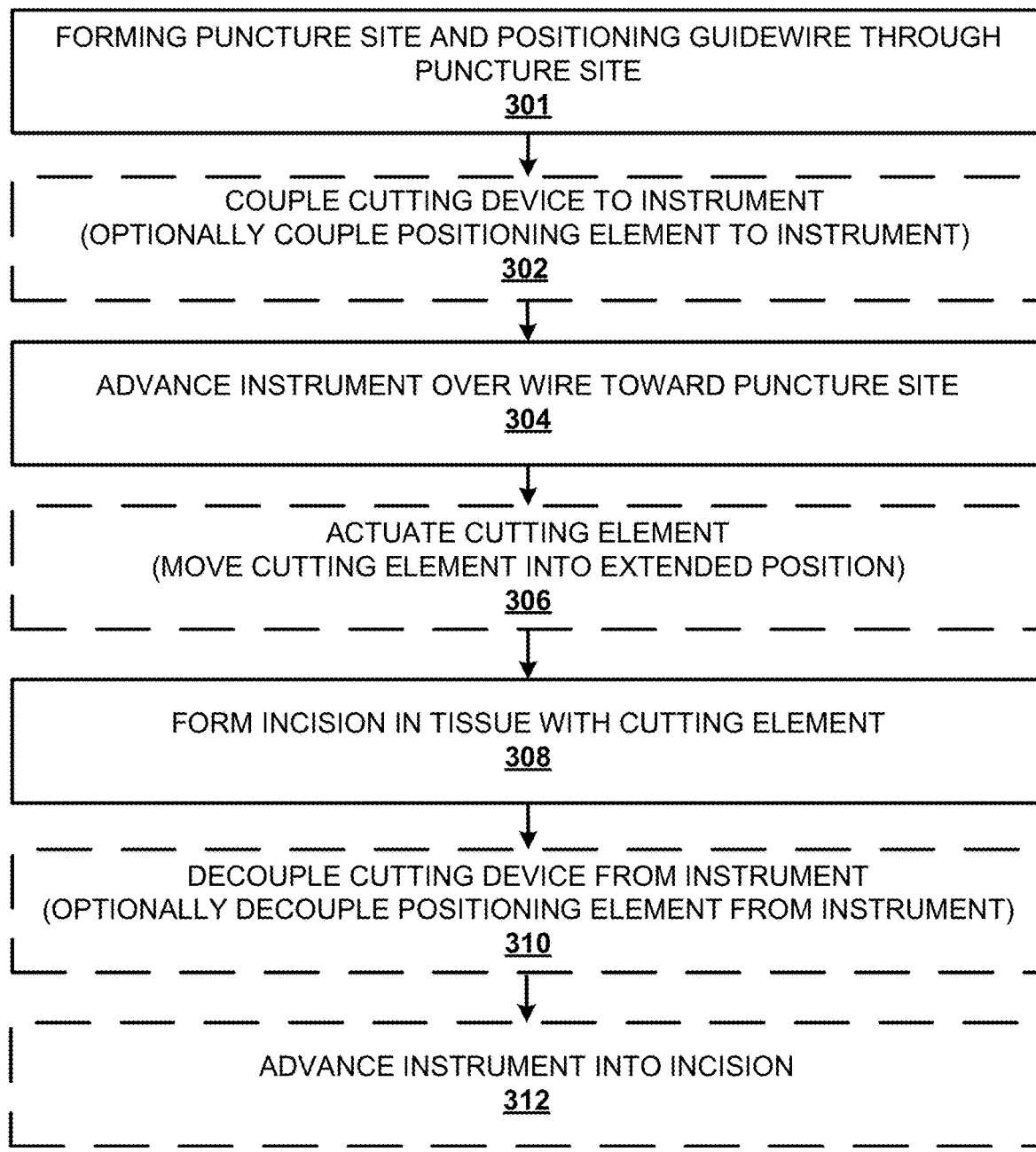
FIG. 3 is a flow diagram illustrating a method of performing a medical procedure on a subject using a cutting device, according to an embodiment.

Referring now to FIG. 3, a method 300 of performing a medical procedure on a subject using a cutting device, such as any of those described herein (e.g., cutting device 100, 200, 500, 1200, and/or 1300), is shown and described.

The method 300 can be a method of forming an incision for receiving an instrument (e.g., instrument 250). The instrument can be, for example, a dilator. The method 300 can include forming, e.g., using a needle, a puncture site in tissue (e.g., skin 170), and advancing a guidewire through the needle into a body lumen, at 301. The needle can be removed, leaving the guidewire positioned traversing the puncture site. The instrument can define a lumen configured to receive the guidewire. The method 300 can optionally include coupling a cutting device to the instrument, at 302. In some embodiments, a positioning element (e.g., positioning element 120, 220 such as a spacer) can also be coupled to the instrument to assist with appropriate positioning of the cutting device on the instrument and to prevent proximal movement of the cutting device relative to the instrument. In some embodiments, each of the cutting device and/or the positioning element can be reversibly coupled to the instrument such that each can be removed (e.g., detached, decoupled) from the instrument, e.g., when moved in a direction lateral to the longitudinal axis (e.g., a central longitudinal axis) of the dilator. In some embodiments, the method 300 may not include coupling the cutting device to the instrument because the instrument may be provided (e.g., packaged, sold, etc.) with the cutting device pre-attached, to, but removable or detachable from, the instrument.

At 304, the method 300 can include advancing the instrument over and along the guidewire toward the puncture site, e.g., until a distal end of the instrument is against a surface of the tissue. At 306, the method 300 optionally includes actuating (e.g., via actuating assembly 104) a cutting element (e.g., 110, 210) of the cutting device, e.g., to move the cutting element from a retracted position to an extended position. In some embodiments, the cutting element can be angled (e.g., to follow a tapered end of the instrument, such as the tapered end of a dilator), and therefore, actuation of the cutting element can cause the cutting element to extend radially inward towards a central longitudinal axis of the instrument. As described above with reference to FIG. 1, actuation of the cutting element can include release of a compressed spring, such that the spring transitions from a compressed state to an uncompressed state to move the cutting element into the extended position. Alternatively, actuation of the cutting element can include moving (e.g., sliding) an actuation element that deploys the cutting element. For example, the cutting element can be moved from the retracted position to the extended position by moving a slider of the cutting device in a distal direction, e.g., using a thumb of a user when the slider is disposed on a side of the cutting device accessible by the thumb. When the cutting element has been actuated (e.g., deployed), the cutting element can be configured to form an incision in the tissue. In some embodiments, the method 300 may not include actuating the cutting element, e.g., because the cutting element is supported on the cutting device in an exposed manner and does not need to be actuated. In such embodiments, the cutting device may include a cap or other component that may shield the cutting element during transport but may be removed from the cutting element prior to use of the cutting device.

The cutting element, when actuated, can form an incision in the tissue, at 308. In some embodiments, the cutting device and the dilator can be advanced toward the tissue after the cutting element has been extended to form the incision. The incision can be formed such that it extends from the puncture site and is sized to receive the instrument. The incision, for example, can be formed to have a length that is substantially equal to the diameter of the instrument. In some embodiments, the cutting device includes a depth control element (e.g., depth control element 108), which can control a distance that the cutting element can extend beyond a distal end of the cutting device and/or a distance that the cutting element can be inserted into the tissue, thereby controlling a depth of the incision. For example, a surface of the cutting device (e.g., a surface of a housing of the cutting device) can be configured to contact the tissue once the cutting element has been inserted a set distance into the tissue. Alternatively or additionally, one or more components of the cutting device may lock to prevent further extension of the cutting element beyond a distal end of the cutting device. In some embodiments, the cutting element can be movable, after forming the incision, from its extended position back to its retracted position.

At 310, the method 300 optionally includes removing (e.g., decoupling, detaching) the cutting device and/or positioning element from the instrument, e.g., by moving the cutting device and/or positioning element in a direction lateral to the longitudinal axis of a body (e.g., body 254) of the instrument.

At 312, the method 300 optionally includes, after forming the incision, advancing the instrument over the guidewire into the incision. In some embodiments, the instrument is advanced until a distal end of the instrument is disposed within the body lumen. In some embodiments, when the instrument is a dilator, the instrument can be removed from the incision, and subsequent, larger instruments can be used to further dilate the subdermal tract to a final dilatation that allows a final catheter to be slid over the guidewire into the body lumen. The catheter can then provide access to the body lumen, e.g., via a lumen of the catheter.

Figure 4:
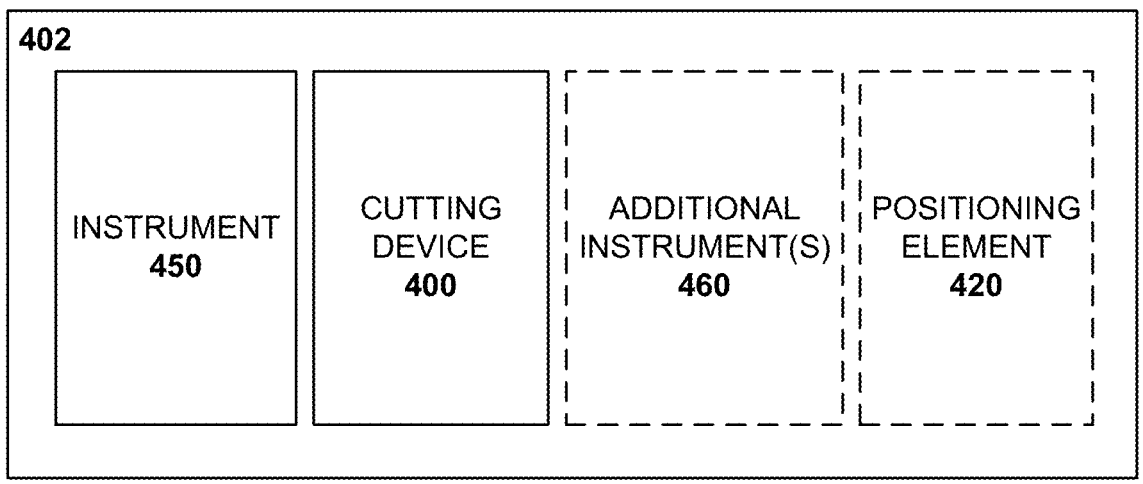
FIG. 4 is a schematic diagram depicting a kit including a cutting device, according to an embodiment.
Figure 5:
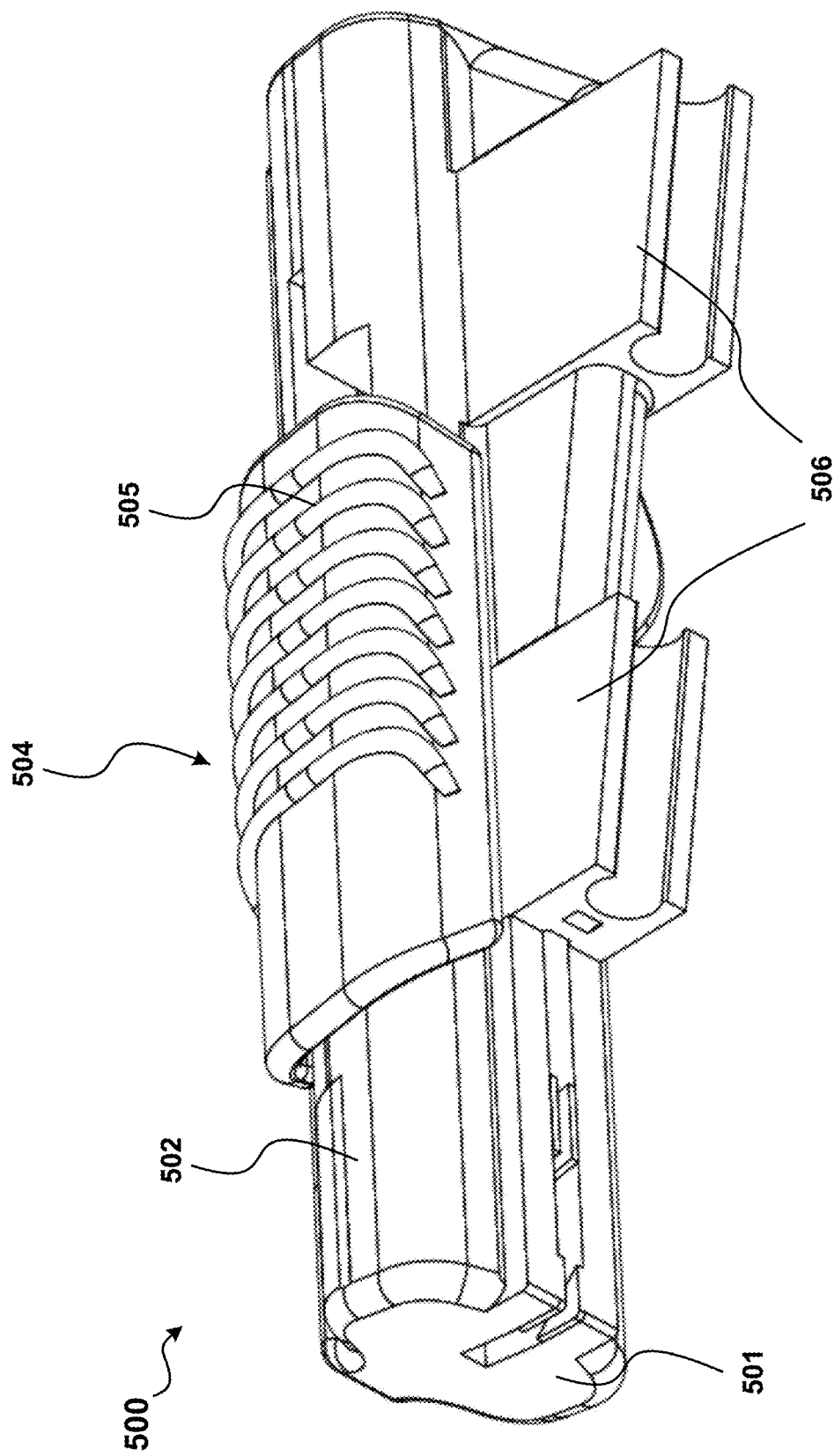
FIG. 5 depicts a perspective view of a cutting device, according to an embodiment.

Referring now to FIG. 4, a schematic diagram depicting components of a surgical system is shown and described. The components depicted in FIG. 4 can be provided in a kit 401, which can be provided to a physician for use during a surgical procedure. The kit 401 can be provided in packaging 402, such as, for example, a box, a bag, etc. The packaging 402 can be configured to keep the components of the surgical system sterile prior to use. The surgical system can include an instrument 450 and a cutting device 400, and optionally, a positioning element 420 and/or additional instrument(s) 460.

The cutting device 400 can be functionally and/or structurally similar to other cutting device described herein (e.g., cutting device 100, 200). For example, in some embodiments, the cutting device can include a cutting element (e.g. cutting element 110, 210) configured to form an incision in tissue.

When included together in packaging 402, the cutting device 400 can be pre-coupled to the instrument 450 at a desired location, e.g., allowing the creation of an incision in tissue. For example, the cutting device 400 can be coupled to the instrument such that a cutting element (e.g., cutting element 110, 210) of cutting device 400 can be configured to form an incision for receiving the instrument 450, e.g., an incision that extends from a puncture site and is sized for receiving the instrument 450. Alternatively, the cutting device 400 and the instrument 450 can be separately placed within the packaging 402, e.g., within separate inner compartments and/or containers.

One or more components of kit 401 can be configured to be disposed after a single use. For example, the cutting device 400 can be configured for one-time use, e.g., the cutting device 400 can include one or more components that lock after a single use.

The instrument 450 can be a dilator, a catheter, a chest tube, or other surgical instrument. The instrument 450, similar to instrument 250 described above, can define a lumen configured to receive a wire such as a guidewire that extends or is otherwise extendable through a puncture site. In some embodiments, the kit 401 can optionally include an appropriately sized guidewire (not shown) for use with the instrument 450. The instrument 450 can include a hub (e.g., similar to hub 252) at a proximal end and body (e.g., similar to body 254). The incision formed by the cutting device 400 can be sized to receive the instrument 450. For example, the incision can have a length that is substantially equal to a diameter of the instrument 450. In some embodiments, the kit 401 can include the instrument 450 having a first diameter, and additional instruments 460 having diameters different than the first diameter. For example, the instrument 450 can be a dilator with a first diameter, and an additional instrument 460 can be a dilator having a diameter greater than the first diameter of the dilator. In such embodiments, the kit 401 can contain a set of dilators that progressively increase in size, e.g., a progressive set of dilators. The dilators can increase in size from (1) a first diameter of the dilator that is configured to couple to the cutting device 400 to (2) a second diameter equivalent to a diameter of the final instrument (e.g., catheter) to be inserted into the incision and into a target vessel. Each of the dilators can be used to dilate the incision to the size of the surgical instrument. In these instances, the cutting device can create an incisional length equal to the diameter of the final dilator/catheter/tube to be inserted.

In some embodiments, the kit 401 can include the positioning element 420, which can be a spacer configured to assist with positioning the cutting device 400 relative to the instrument 450. Similar to positioning elements 120, 220, as described above, positioning element 420 can extend longitudinally along a length of the instrument 450 between a proximal portion (e.g., hub) of the instrument 450 to where the cutting device 400 couples to the instrument 450, thereby setting a location of the cutting device 400 relative to the proximal portion of the instrument 450 and preventing proximal movement of the cutting device 400 relative to the instrument 450. When included together in kit 401, the positioning element 420 can be pre-coupled to the instrument 450 along with the cutting device 400 such that the instrument 450 and the cutting device 400 are ready for use. Alternatively, the positioning element 420, cutting device 400 and instrument 450 can be included separately in kit 401 (e.g., in separate compartments or packages), such that a physician prior to and/or during a surgical operation must attach the positioning element 420 and the cutting device 400 to the instrument 450, permitting the cutting device 400 to form an incision in tissue during the operation.

Figure 7:
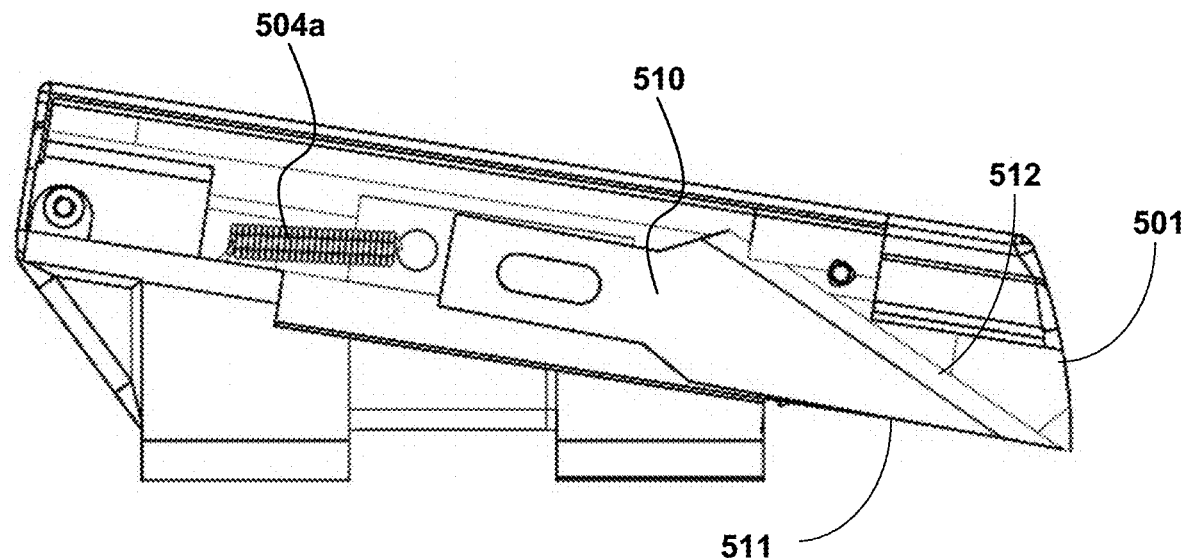
FIG. 7 depicts a cross-sectional view of the cutting device shown in FIG. 5, taken along A-A as shown in FIG. 6, according to an embodiment.
Figure 8:
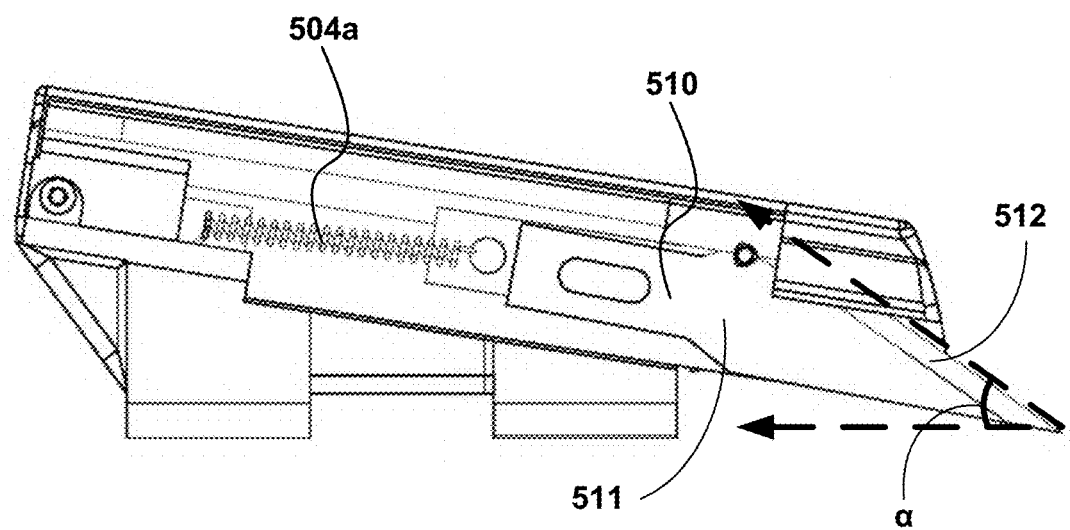
FIG. 8 depicts a cross-sectional view of the cutting device shown in FIG. 5, taken along A-A as shown in FIG. 6, according to an embodiment.
Figure 9:
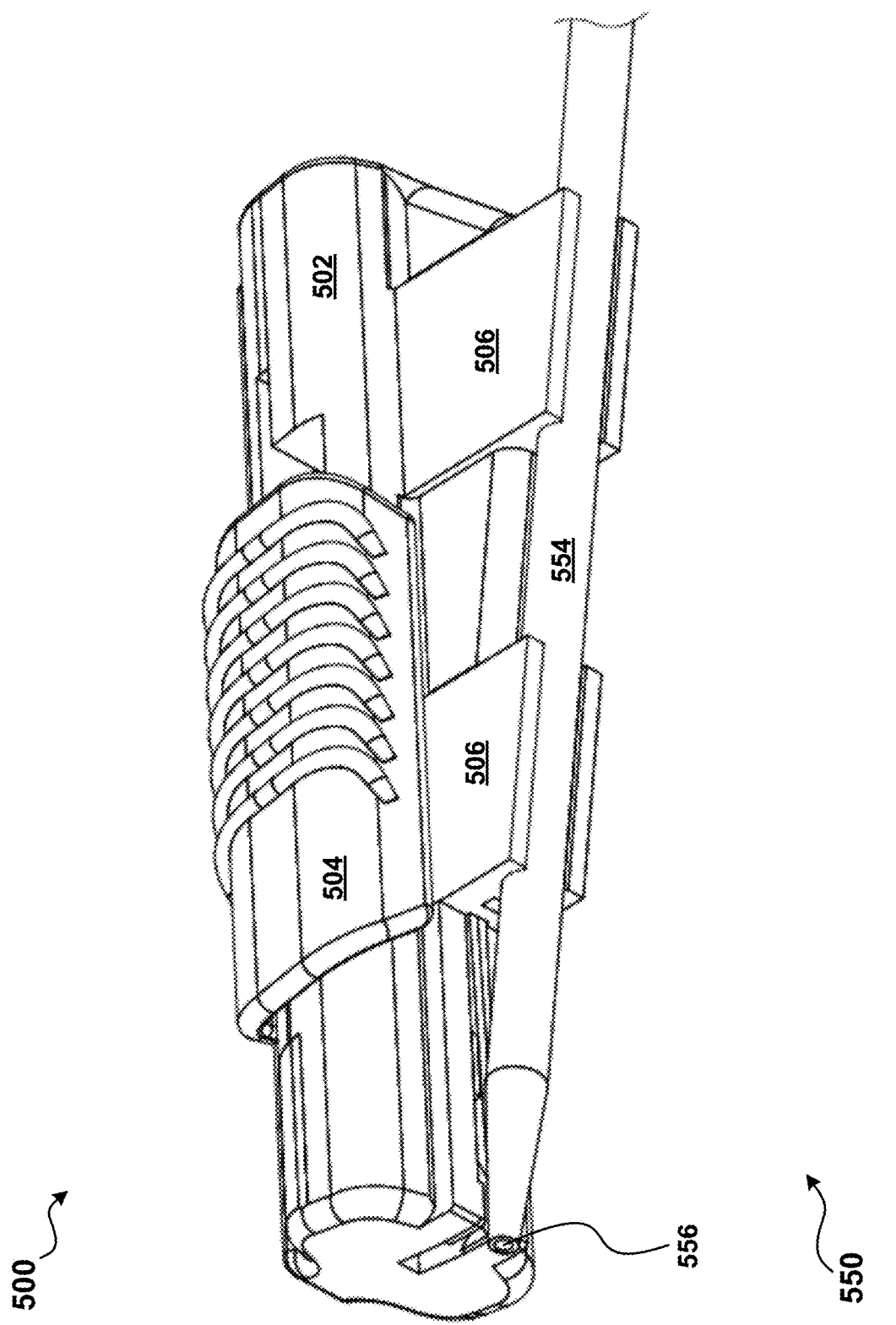
FIG. 9 depicts a perspective view of the cutting device shown in FIG. 5 while attached to a medical device, according to an embodiment.
Figure 10:
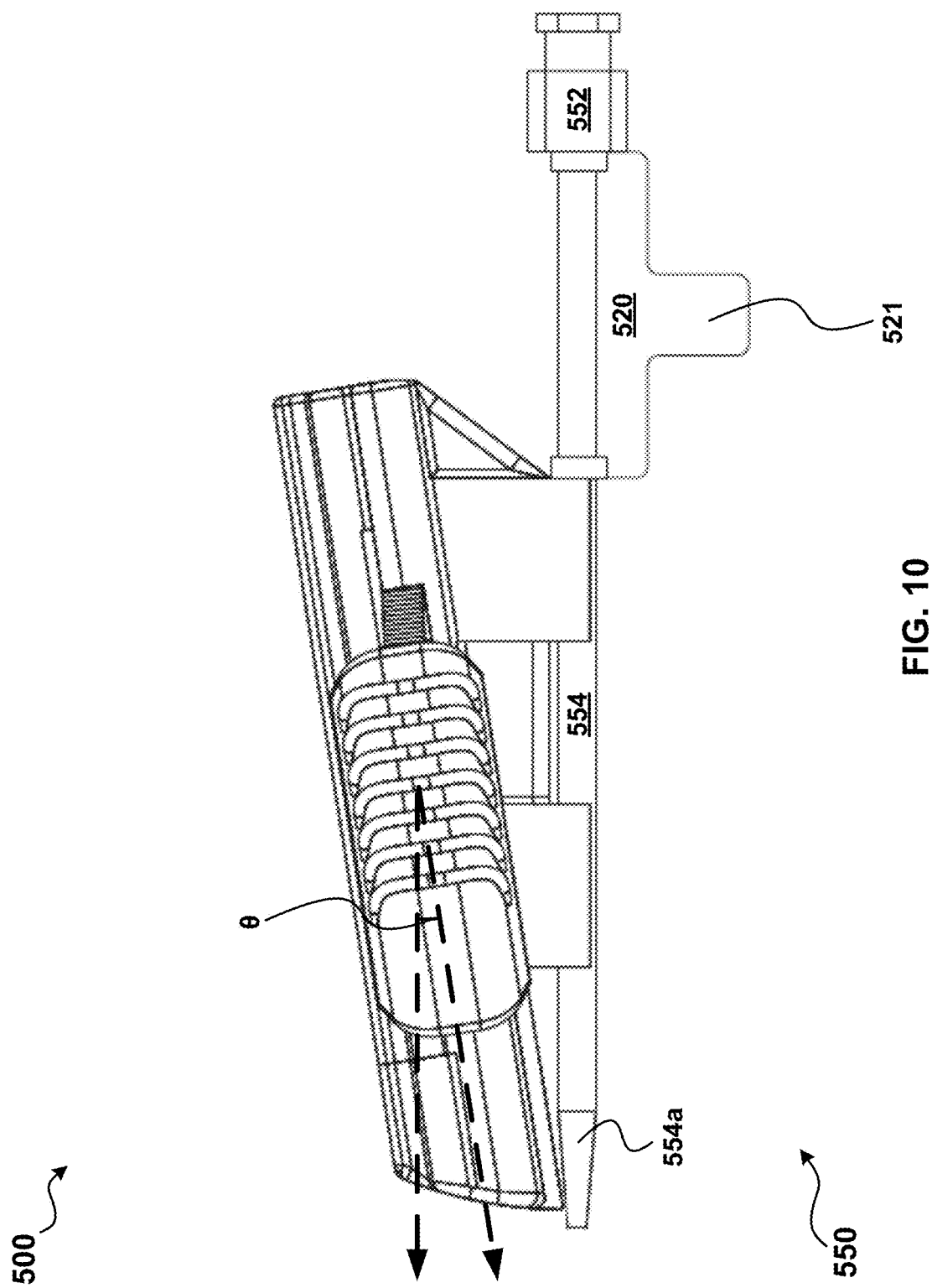
FIG. 10 depicts a side view of the cutting device shown in FIG. 5 while attached to a medical device, according to an embodiment.
Figure 11:
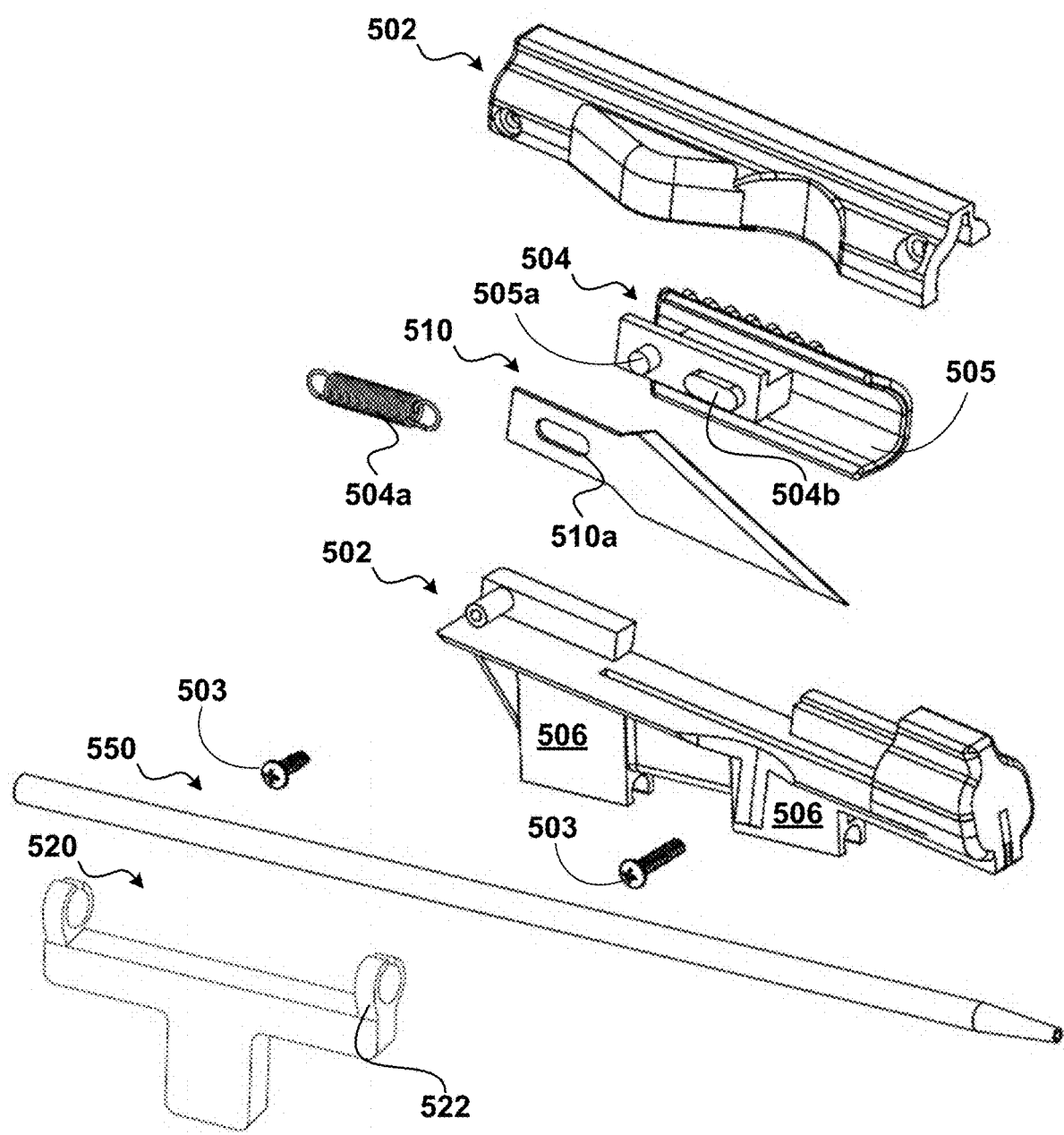
FIG. 11 depicts an exploded view of the cutting device shown in FIG. 5, according to an embodiment.

Referring now to FIGS. 5-10, various views of an example cutting device 500 are shown and described. The cutting device 500 can include components that are structurally and/or functionally similar to other cutting devices described herein, e.g., cutting devices 100 and 200. For example, the cutting device 500 can include a housing 502, an actuation assembly 504, a cutting element 510, a coupling mechanism 506, a depth control element implemented as a tissue contact surface 501, a positioning element 520, and a coupling mechanism 522. The cutting device 500 can be used with a medical device or instrument 550, as depicted in FIGS. 9 and 10. The medical device 550, similar to other medical devices described herein (e.g., medical device 250), can include a hub 552 and a body 554. The medical device 500 can be implemented as a dilator that includes a tapered distal end 554*a*. As shown in FIG. 9, the medical device 550 can define a lumen 556 configured to receive a wire that extends or is otherwise extendable through a puncture site.

As shown in FIGS. 9-10, the cutting device 500 can be reversibly coupled to the medical device 550 via the coupling mechanism 506, similar to that described with respect to the reversible coupling between the cutting device 200 and the instrument 250 via the coupling mechanism 206. Further, the cutting device 500 can be designed such that, in a deployed position, a base (e.g., bottom edge 511 depicted in FIG. 8 and 9) of the cutting element 510 extends along a distal end of the instrument 550 in contact with an outer surface of the instrument 550, and in particular, extends radially inwardly towards a central longitudinal axis of the instrument 550, e.g., at an angle θ as shown in FIG. 10. The angle θ can be equal to or greater than an angle of the tapered distal end 554*a* of the instrument 550, with respect to the longitudinal axis of the instrument 550. In some embodiments, when the cutting element 510 is extended, a distal end of the cutting element 510 can terminate at (or substantially near) a distal end of the instrument 550. The size of the incision formed by the cutting element can be dependent on an angle α of an outer cutting edge 512 of the cutting element 510 and a length that the cutting element 510 extends from a distal surface 501 of the cutting device 500, as further described below.

Figure 6:
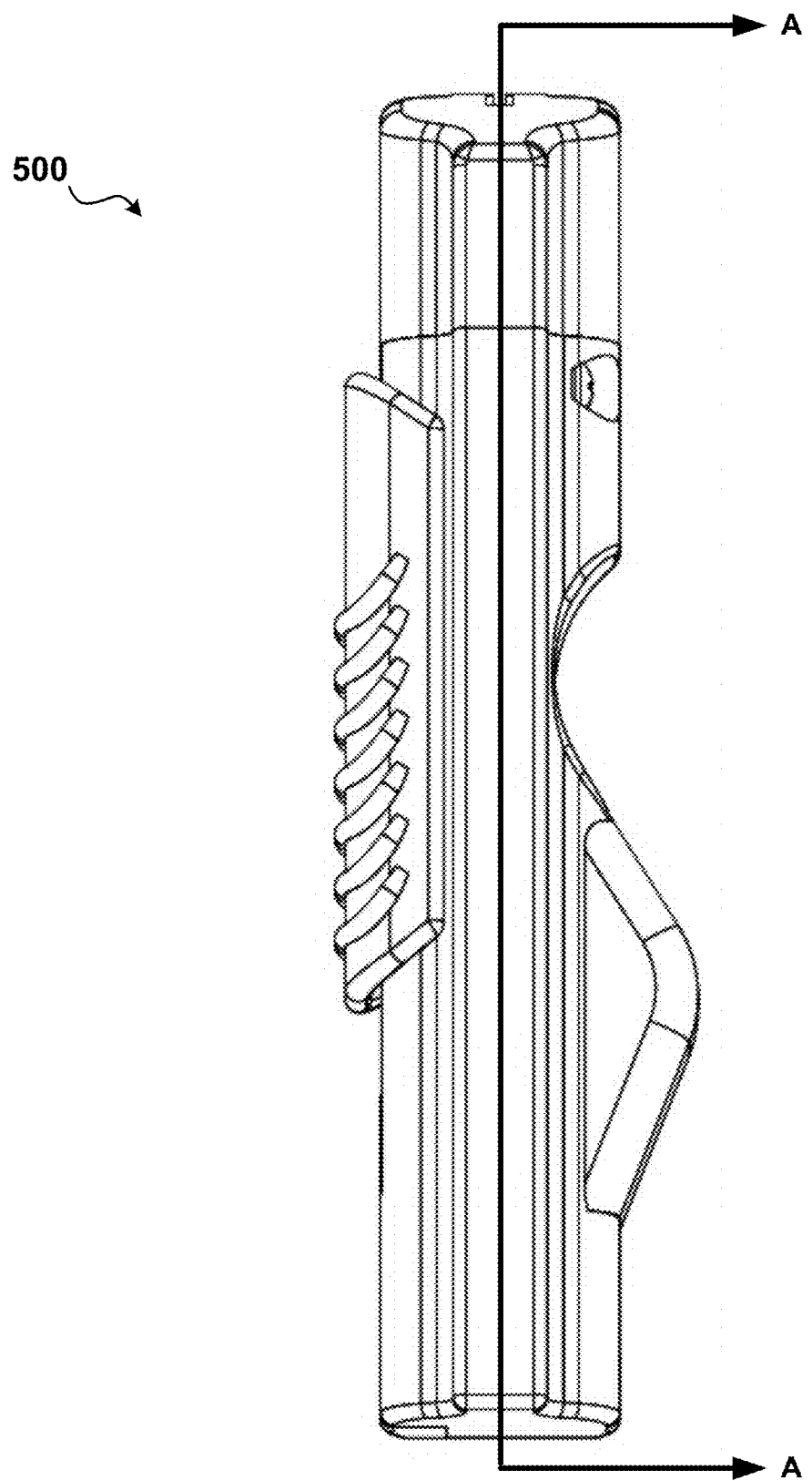
FIG. 6 depicts a top view of the cutting device shown in FIG. 5, according to an embodiment.

The housing 502 can include multiple housing components that are held together via one or more fasteners, e.g., screws 503, and/or adhesive. The housing 502 can define a volume, recess, or area for housing the cutting element 510 in a retracted or undeployed position, such as shown in FIG. 7. For example, the cutting element 510 can be retracted for shielding such as behind a distal surface 501 of the cutting device 500. As shown in FIG. 6, the housing 502 can be ergonomically shaped to enable a user (e.g., a physician) that is operating the device to hold the housing 502 in a single handle and to actuate the actuation mechanism 504 to deploy the cutting element 510, i.e., the move the cutting element 510 from its undeployed position (depicted in FIG. 7) to its deployed position (depicted in FIG. 8). In some embodiments, different configuration(s) of the housing 502 can be suited for use by right- and left-handed users.

The cutting element 510 can include an inner edge 511 and an outer cutting edge 512, and can be designed to be movable via the actuation assembly 504 between a retracted position, such as shown in FIG. 7, and an extended position, such as shown in FIG. 8. The cutting element 510 can include a locking mechanisms (e.g., a lock as described with reference to FIGS. 1-3, and internal surfaces as further described below) that prevents the cutting element 510 from extending beyond the retracted position (e.g., further into the housing 502) or the extended position (e.g., further distal to the housing 502). As such, the retracted position is a fully retracted position and the extended position is a fully extended position. In the retracted position, the cutting element 510 can be fully disposed within the housing 502. In the extended position, a distal end of the cutting element 510 can terminate at (or substantially near) the distal end of the instrument 550. In some embodiments, a portion of the inner edge 511 can extend substantially along the tapered distal end of the instrument 550 in contact with an outer surface of the instrument 550. The cutting element 510 can be moved from the retracted position to the extended position and vice-versa. For example, such as shown in FIGS. 7-8, the cutting element 510 can be moved to the extended position by actuation of the actuation assembly 504, implemented as a sliding component 505. The sliding component 505 can be moved distally along a length of the cutting device 500 to move the cutting element 510 into the extended position. In all positions ranging from the retracted position to the extended position, the inner edge 511 of the cutting element 510 and a distal end of the cutting element 510 are disposed radially outward from the lumen of the instrument 550. Stated differently, the cutting element 510 is configured to extend along the instrument 550 in contact with its outer surface but to not extend radially inward of an outer surface of the instrument 550. The cutting element 510 can therefore form an incision that extends radially outward from a puncture site or a wire disposed in the lumen of the instrument 550.

As depicted, the sliding component 505 can be attached (e.g., via a knob or protrusion 505a) to an elastic component such as a spring 504a that is expandable to accommodate the movement of the sliding component 505 and the cutting element 510 in the distal direction (e.g., to move the cutting element 510 into its extended position). When expanded, the spring 504a can exert a force upon the sliding component 505, such that when sliding component 505 is released, the spring 504a can automatically revert to its resting position and retract the cutting element 510 back into its retracted position in the housing 502.

The actuation assembly 504 can be designed to actuate the cutting element 510 from a retracted position to a deployed (e.g., extended) position to form an incision in and through skin (e.g., skin 170). For example, the actuation assembly 504 implemented as the sliding component can include an interface element 504b (e.g., a protrusion) designed to interface with (e.g., engage with) an interface element 510a (e.g., a recess) of the cutting element 510, to thereby actuate and move the cutting element 510 longitudinally along the housing 502.

As described, the outer cutting edge 512 can be configured to cut tissue to form an incision. In some embodiments, the inner edge 511 in addition to the outer cutting edge 512 can be configured to cut tissue to form the incision. Since a distal end of the inner edge 511 extends along a distal end of the instrument 550 (e.g., a tapered end of a dilator), i.e., is immediately adjacent or next to the distal end of the instrument 550, having both the inner edge 511 and outer edge 512 be configured to cut tissue can further reduce the risk of leaving a skin bridge.

In some embodiments, the cutting device 500 may not include a spring, such as spring 504a. In such embodiment, the user (e.g., physician) can manually retract the cutting element 510 back into the housing 502 after forming the incision by moving the sliding component 505 back in a proximal direction. While the cutting device 500 is depicted with an actuation assembly including a sliding component 505, it can be appreciated that any number or type of actuation mechanisms can be used, e.g., including a button, tab, lever, and the like, which can be actuated by a user to deploy the cutting element 510, such as described above with reference to cutting device 100. For example, the actuation assembly 504 can alternatively include a trigger that can be actuated to release a pre-loaded or compressed spring or other elastic component that can generate a force to deploy and/or retract the cutting element 510. In some embodiments, the actuation assembly 504 can alternatively include hydraulic or pneumatic mechanisms for deploying and/or retracting the cutting element 510.

The depth control element can be designed to limit a depth of insertion or deployment of the cutting element 510. In an embodiment, the depth control element can be implemented as a distal surface 501 of the cutting device 500. The distal surface 501 of the cutting device 500 can be configured to contact a tissue surface and prevent further insertion of the cutting element 510 into the tissue. In particular, the cutting device 500 mounted on the instrument 550 and with the cutting element 510 extended can be slid down a length of a guidewire until the distal surface 501 contacts the tissue surface and prevents further insertion of the cutting element 510 into the tissue. The size of the incision can be controlled by a distance that the outer cutting edge 512 extends from the distal end 501 of the cutting device 500 and an angle α that the outer cutting edge 512 is angled with respect to the longitudinal axis of the instrument 550. In other embodiments, the depth control element can be implemented as a surface that interacts with a surface of at least one of the cutting element 510 and/or the sliding component 505 of the actuation assembly 504 to control distal movement of the cutting element 510. For example, the depth control element can be an internal surface of the housing 502 that engages a surface of the sliding component 505 once the sliding component 505 has extended the cutting element 510 a set distance from its retracted position. Alternatively, the depth control element can include a stopper designed to interface with a surface of the cutting element 510 by abutment to control translation and a depth of insertion of the cutting element 510. In some embodiments, the depth control element can be integrated into and/or coupled to the housing 502 and/or cutting element 510.

The coupling mechanism 506 can include one or more fasteners or couplings designed to reversibly couple the housing 502 to the instrument 550, such as that shown in FIGS. 9-10. For example, the coupling mechanism 506 can include a flexible component such as a clip or clasp that is designed to reversibly couple the housing 502 of the cutting device 500 to the instrument 550 such as by gripping around the body 54 of the instrument. The coupling mechanism 506 can be configured to couple to the instrument 550 from a lateral direction, i.e., by moving the housing 502 in a direction toward the longitudinal axis of the instrument 550, and similarly to decouple from the instrument 550 in a lateral direction. The coupling mechanism 506 can be integrated into or otherwise used in conjunction with the housing 502 in any suitable manner so as to enable and facilitate reversible coupling of the housing 502 to the instrument 550, such as described herein. Once coupled to the instrument 550, the coupling mechanism 506 can generate sufficient friction against a surface of the body 554 of the instrument 550 to prevent movement (e.g., sliding and/or rotation) of the cutting device 500 relative to the instrument 550. As depicted in FIGS. 9 and 10, the coupling mechanism 506 can include multiple attachment points to reduce the risk of movement due to a torsional force. In some embodiments, the coupling mechanism 506 can be configured to couple the housing 502 to a specific size of instrument, e.g., a dilator having a specific diameter and length. In other embodiments, the coupling mechanism 506 can be adjustable (e.g., via tightening and/or loosening of a screw or other adjustment mechanism, or due to a malleability of the coupling mechanism) to adapt the coupling mechanism 506 for use with different sized instruments.

The positioning element 520 can be used with the cutting device 500 to maintain the housing 502 in a fixed spatial relation with respect to the medical device 550. For example, the positioning element 520 can be implemented as a spacer having a handling tab 521 to facilitate coupling (e.g., by a user) of the positioning element 520 with the instrument 550, e.g., via coupling mechanism 522. The spacer can be placed such that it extends from the hub 552 (e.g., is adjacent to the hub 552) to a proximal end of the housing 502, thereby defining a set spacing between the hub 552 and the housing 502, as shown in FIG. 10. The spacer can be configured for use with a specific size of the instrument 550, e.g., a dilator having a specific diameter and length.

The coupling mechanism 522 can be designed to reversibly couple the positioning element 520 to the instrument 550. For example, the coupling mechanism 522 can include a flexible component such as a clip or clasp that is designed to removably couple the positioning element 520 to the instrument 550 such as by interference fit, press fit, friction fit, and the like (e.g., by gripping around the body 554 of the instrument 550. The coupling mechanism 522 can be integrated into or otherwise used in conjunction with the positioning element 520 so as to enable and facilitate reversible coupling of the positioning element 520 to the instrument 550, such as described herein. The positioning element 520 and the housing 502 can be separately and individually attachable to and removable from the instrument 550.

In use, cutting device 500 including the housing 502 and the positioning element 520 can be coupled (e.g., attached) to the body 554 of the instrument 550. The instrument 550 can be slid down a length of a guidewire that is positioned in a puncture site, e.g., a puncture site formed as part of a surgical procedure using the Seldinger technique. The instrument 550 can be slid down the guidewire until a distal end of the instrument 550 is positioned adjacent to the skin with the puncture site. The cutting element 510 can be positioned in a retracted position (as shown in FIG. 7) while the instrument 550 is slid down a length of the guidewire. Once the instrument 550 is in position against the skin, the cutting device 500 can then be actuated, e.g., by sliding the sliding component 505 toward the puncture site to form an incision with the cutting element 510 that extends from the puncture site and is sized to receive the instrument 550. Optionally, the cutting element 510 can be retracted back into the housing 502, and the housing 502 and/or the positioning element 520 can be removed (e.g., decoupled, detached) from the instrument 550 and set aside. The instrument 550 can then be inserted into the incision, e.g., to dilate the tissue below the incision and/or be placed within a body lumen to provide vascular access to the body lumen.

Figure 12A:
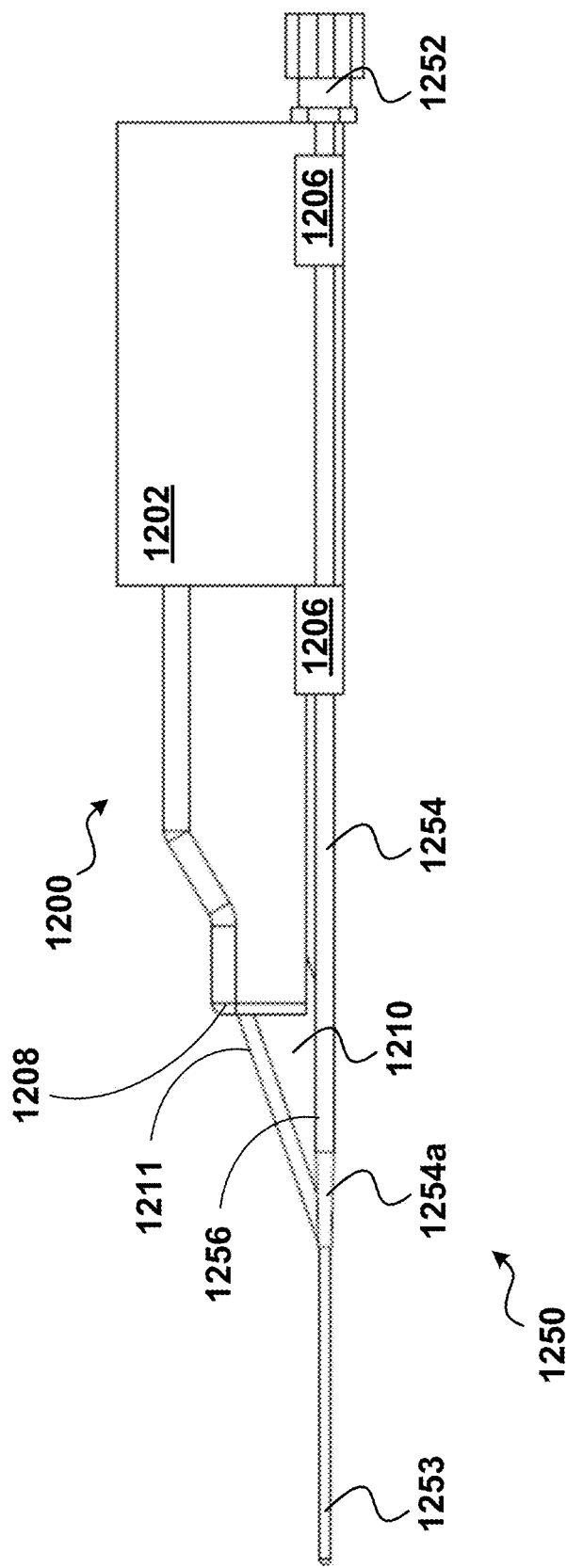
FIG. 12A depicts a side view of a cutting device, according to an embodiment.
Figure 12B:
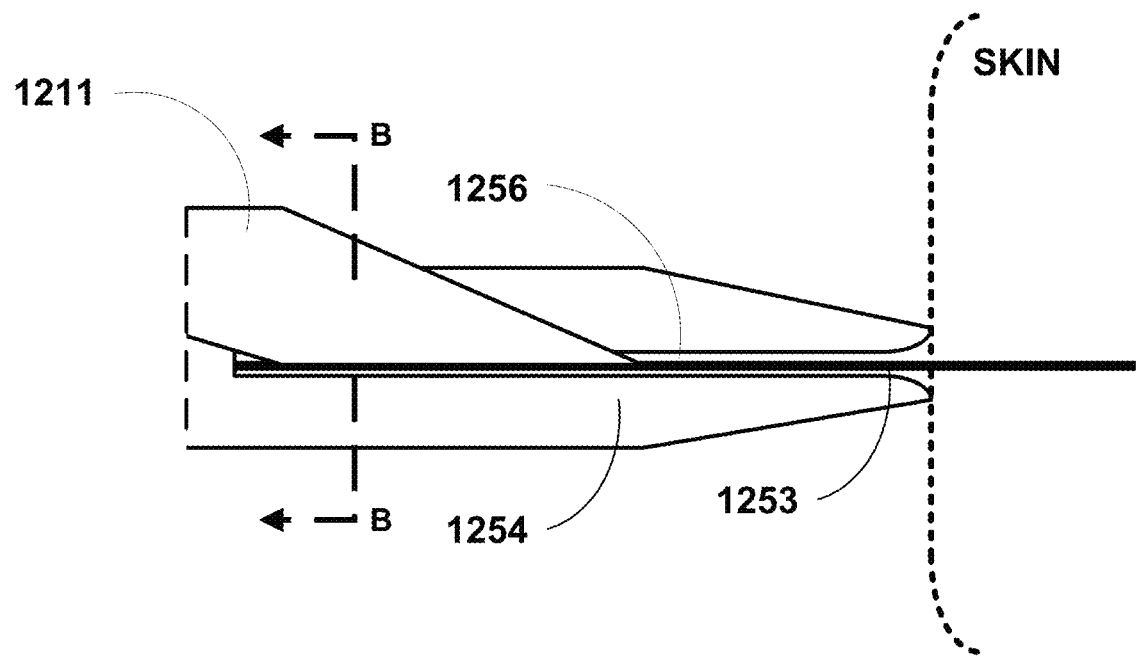
FIG. 12B depicts an enlarged view of a distal end of an instrument used with the cutting device depicted in FIG. 12A, according to an embodiment.
Figure 12C:
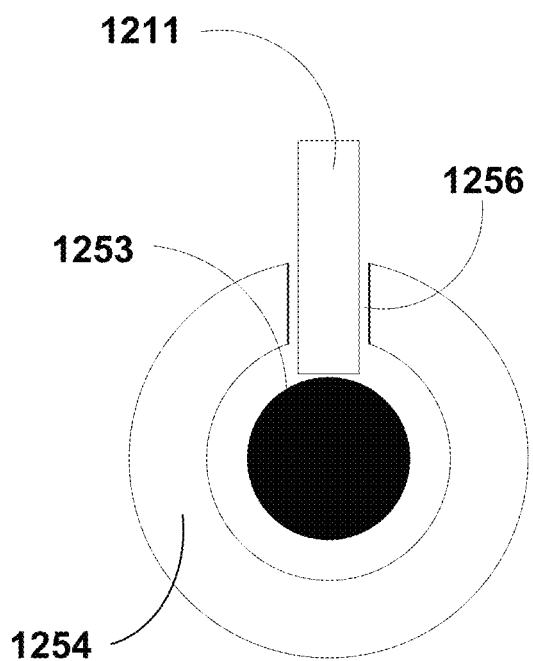
FIG. 12C depicts a cross-sectional view taken along a line B-B in FIG. 12B.

Referring now to FIGS. 12A-12C, views of another example cutting device 1200 are shown and described. FIG. 12A depicts a side view of the cutting device 1200 coupled to an instrument 1250 (e.g., a dilator). FIG. 12B schematically illustrates a distal end of the cutting device 1200 and the instrument 1250. And FIG. 12C schematically illustrates a cross-sectional view of a distal end portion of the cutting device 1200 and the instrument 1250. The cutting device 1200 can include components that are structurally and/or functionally similar to other cutting devices described herein. For example, the cutting device 1200 can include a housing 1202, a cutting element 1210, and a coupling mechanism 1206. The cutting device 1200 can be used with the instrument 1250, similar to other instruments described herein.

As depicted in FIG. 12A, the instrument 1250 can be implemented as a dilator having a body 1254 that includes a tapered distal end 1254a, and a hub 552 at a proximal end. The instrument 1250 can define a lumen configured to receive a wire such as guidewire 1253 that extends or is otherwise extendable through a puncture site. In addition, the instrument 1250 can include a slot or opening 1256 that extends along a distal portion of the instrument 1250 for receiving the cutting element 1210 therethrough, as further described below.

The cutting device 1200 can be configured to reversibly couple to the instrument 1250 and can include a proximal end configured to abut the hub 1252 of the instrument 1250 when coupled thereto, as described herein. In some embodiments, the cutting device 1200 may be designed to move or slide longitudinally along a body 1254 of the medical device 1250.

The housing 1202 can support the cutting element 1210. For example, the housing 1202 can include a clamp, protuberance, knob, bump, or other attachment mechanism for holding and supporting the cutting element 1210. The cutting element 1210 can include an inner edge (not depicted) and an outer cutting edge 1211. In some embodiments, the inner edge in addition to the outer cutting edge 1211 can be a cutting edge configured to cut tissue. The cutting element 1210 can be translated along the instrument 1250 by translation of the housing 1202 along the instrument 1250, such that the inner edge moves along a length of the slot 1256 in the instrument 1250. The cutting element 1210 can be translated distally along a length of the instrument 1250 such that it extends into tissue. In some embodiments, the housing 1202 can be designed to be slid or translated along the instrument 1250 by manually applied force (e.g., via a hand of a user).

As depicted in FIGS. 12B and 12C, the slot 1256 enables a portion of the cutting element 1210 (e.g., an inner edge of the cutting element 1210) to extend into an inner lumen of the instrument 1250 such that the cutting element 1210 abuts or is near the wire 1253. The cutting element 1210 can then be slid along the slot 1256 in a distal direction to form an incision that extends from a puncture site in which the wire 1253 is disposed. By enabling the cutting element 1210 to extend into the inner lumen of the instrument 1250 to the wire 1253, the slot 1256 prevents the formation of a skin bridge. As depicted in FIG. 12C, the slot 1256 can have a width that is sufficiently large to permit the cutting element 1210 to extend into the inner lumen of the instrument 1250 but less than a diameter of the wire 1253 such that the wire 1253 cannot exit from the inner lumen of the instrument 1250 via the slot 1256.

In some embodiments, the cutting device 1200 can include a depth control element 1208 that is designed to limit a depth of insertion or deployment of the cutting element 1210. For example, the depth control element 1208 can include a surface of a protrusion (e.g., a protuberance, knob, bump, etc.) designed to contact the skin of a subject to limit further insertion of the cutting element 1210 into the skin. The depth control element 1208 can be integrated into and/or coupled to the housing 1202. Alternatively, the depth control element 1208 can be integrated into and/or coupled to the cutting element 1210.

The coupling mechanism 1206 can reversibly couple the housing 1202 to the instrument. For example, the coupling mechanism 1206 can include a flexible component such as a clip or clasp that is designed to removably couple the housing 1202 to the instrument 1250 such as by interference fit, press fit, friction fit, and the like. The coupling mechanism 1206 can be integrated into or otherwise used in conjunction with the housing 1202 so as to enable and facilitate reversible coupling of the cutting device 1200 to the instrument 1250, such as described herein. In some embodiments, for example, the coupling mechanism 1206 can include two attachment points to prevent movement of the cutting device 1200 with respect to the instrument 1250 due to torsional forces.

A proximal portion of the cutting device 1200 can function as a positioning element, e.g., be designed to maintain the housing 1202 in a fixed spatial relation with respect to the instrument 1250. For example the proximal portion of the housing 1202 can extend to the hub 1252 of the instrument 1250 to define a spacing between the hub 1252 and the cutting element 1210 and to thereby ensure specific positioning of the cutting device relative to a proximal end of the instrument 1250.

Figure 13:
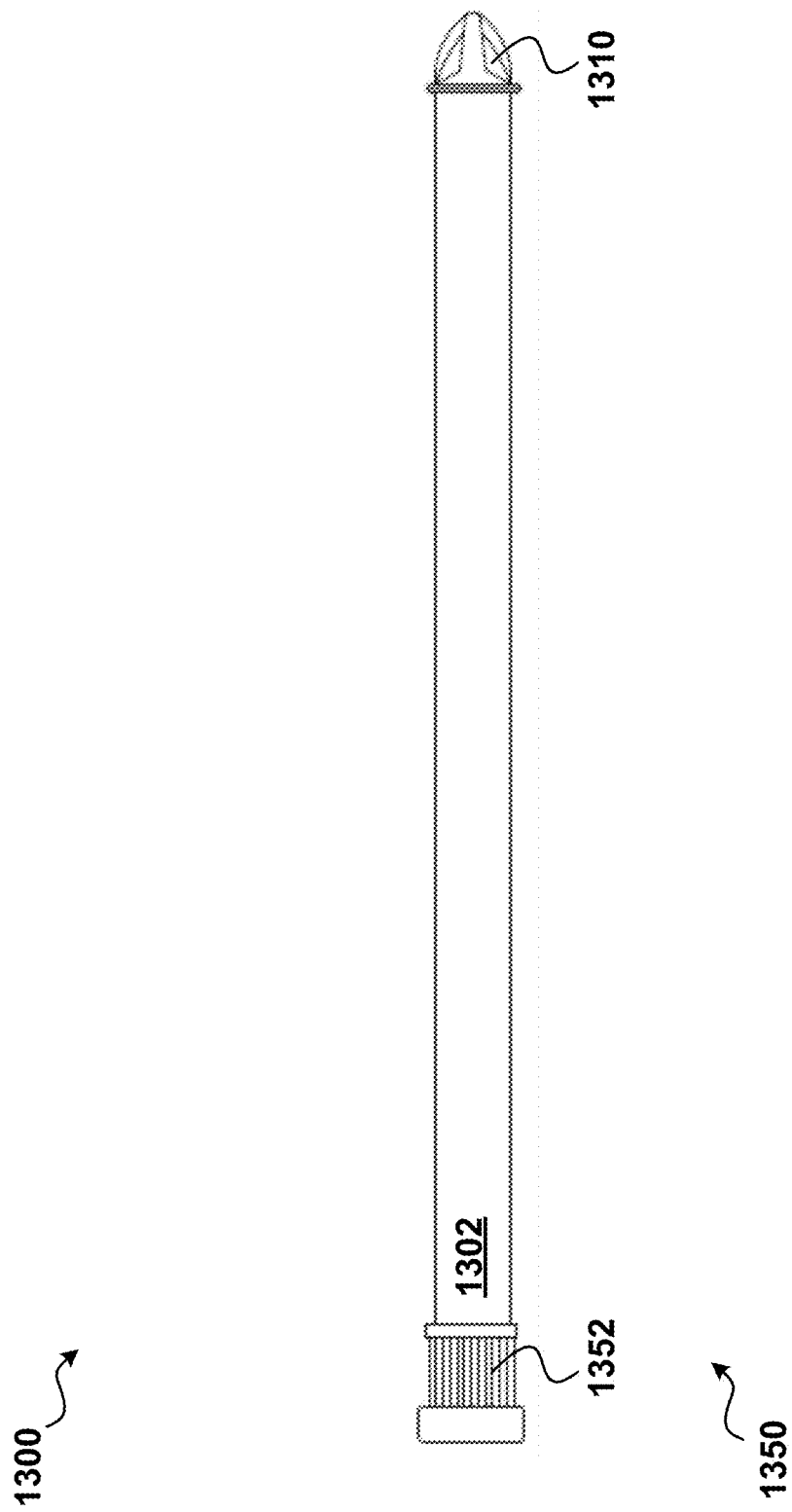
FIG. 13 depicts a side view of a cutting device, according to an embodiment.
Figure 14B:
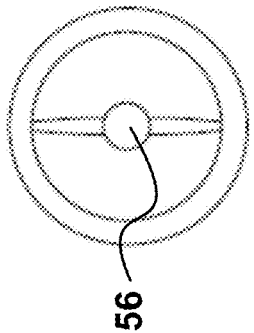
FIGS. 14A-14C depict enlarged views of a distal end of the cutting device shown in FIG. 13, according to an embodiment.
Figure 14A:
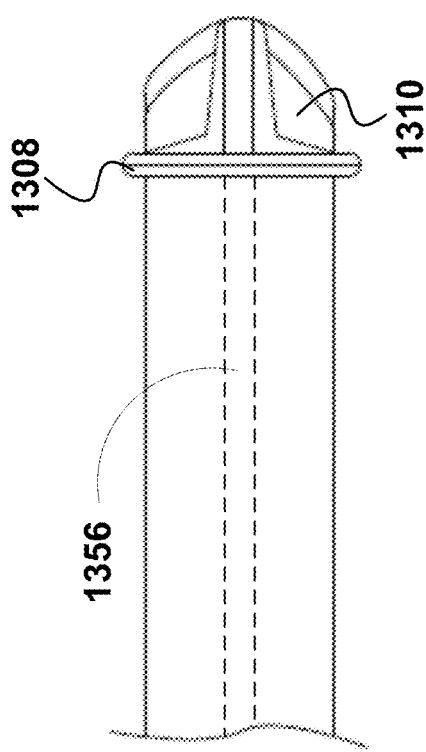
Figure 14C:
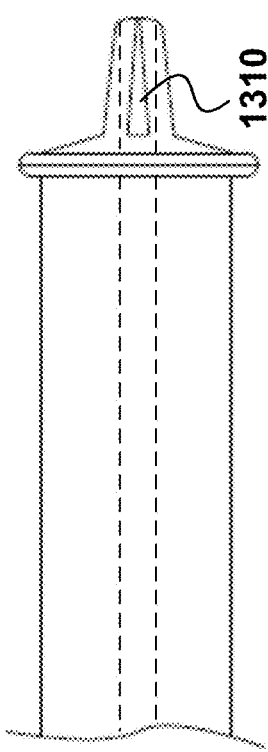

Referring now to FIGS. 13-14C, various views of another example cutting device 1300 are shown and described. The cutting device 1300 can be implemented as an instrument (e.g., a dilator) that includes one or more cutting elements 1310. The cutting device 1300 can include components that are structurally and/or functionally similar to other cutting devices described herein (e.g., cutting device 100, 200, etc.). For example, the cutting device 1300 can include a housing 502, a cutting element 1310, and a depth control element 1308. Similar to other dilators described herein, the cutting device 1300 can include a proximal hub 1352 and an elongate body (e.g., housing 1302) that defines a lumen 1356 for receiving a guidewire that extends or is otherwise extendable through a puncture site.

The cutting device 1300 is designed to receive a guidewire (e.g., wire 1353) within the lumen 1356 of the device and to slide along a length of the guidewire. The housing 1302 at its distal end can support one or more cutting element(s) 1310. Each of the cutting element(s) 1310 can include an outer cutting edge. The outer cutting edge can be configured to form an incision in tissue, where the incision extends from a puncture site in which the guidewire is disposed. The outer cutting edges can be configured to form a continuous incision that is symmetrically disposed about a puncture site. As depicted in FIGS. 14A and 14B, the cutting element(s) 1310 are configured as flat blades.

The cutting device 1300 can include a depth control element 1308 that is designed to control a depth of insertion of the cutting element(s) 1310. For example, the depth control element can include a stopper (e.g., a protuberance, knob, bump, etc.) designed to contact a surface (e.g., skin or tissue of a subject) to limit further insertion of the cutting element(s) 1310 into the tissue. The depth control element 1308 can be integrated into and/or coupled to the housing 1302 and/or cutting element(s) 1310.

Figure 15:
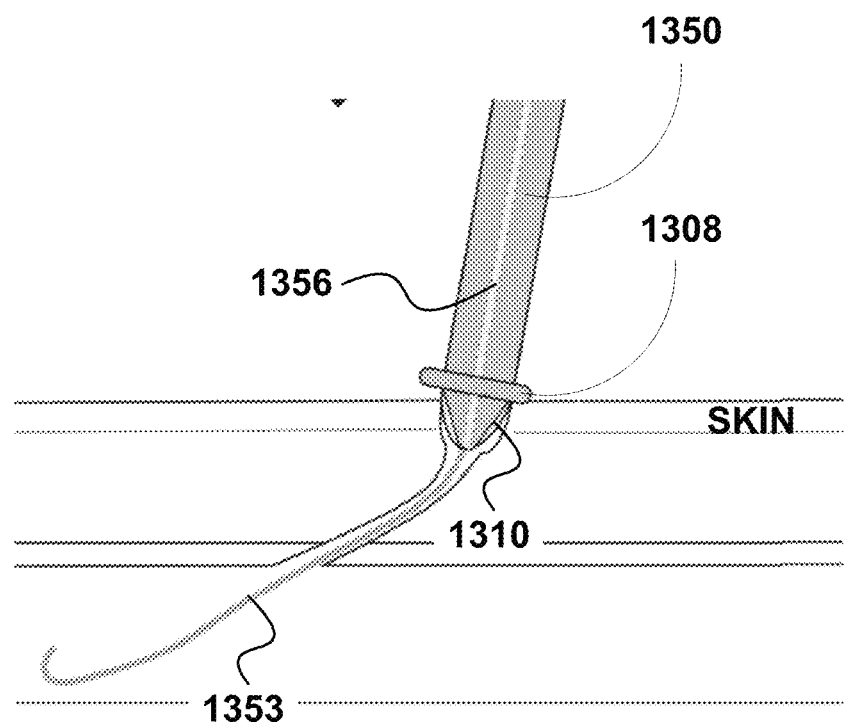
FIG. 15 depicts a view of a distal end of the cutting device shown in FIG. 13 forming an incision around a guidewire, according to an embodiment.

FIG. 15 depicts the cutting device 1300 being used to form an incision in skin. After a wire 1353 has been positioned in a puncture site formed in the skin, the cutting device 1300 can be slid down along a length of the wire 1353 until the depth control element 1308 of the cutting device 1300 contacts a surface of the skin (as depicted in FIG. 15). The cutting element 1310 of the cutting device 1300 can form an incision in the skin that is sized according to a position of the depth control element 1308 relative to a distal end of the cutting device 1300. As the cutting elements 1310 are adjacent to the lumen 1356 of the cutting device 1300 at its distal end, the cutting elements 1310 form an incision that extends from the puncture site without a skin bridge.

Referring now to FIGS. 16A-16D, various views of an example cutting device 1600 are shown and described. The cutting device 1600 can include components that are structurally and/or functionally similar to any of the other cutting devices described herein, e.g., cutting devices 100, 200, 500, 1200, 1300. For example, the cutting device 1600 can include a housing 1602, an actuation assembly 1604, a cutting element 1610, a coupling mechanism (not depicted), a depth control element (not depicted), and/or a positioning element (not depicted). The cutting device 1600 can be used with a medical device or instrument (not depicted), such as a dilator, a catheter, or any others described herein.

The cutting element 1610 can include a single or multiple edges that are formed as cutting edges, which can be configured to cut tissue to form an incision. For example, in an embodiment, both an inner and outer edge of the cutting element 1610 can be cutting edges. Having both inner and outer edges be formed as cutting edges can reduce a risk of leaving a skin bridge. The actuation assembly 1604 can include a guide 1604B and a follower 1604A. The follower 1604A can be configured to be attached to or fixed, mated, or coupled, with the cutting element 1610 in any suitable manner. The actuation assembly 1604 can also include an actuator (e.g., a slider, button, tab, lever, not depicted) that can be moved (e.g., slid along a length of the housing 102) such as by a user. In some embodiments, the guide 1604B and the follower 1604A can be configured to transform movement of the actuator (e.g., caused by an applied force, e.g., by a user) into a combination of linear and lateral motion of the cutting element 1610. In some embodiments, the guide 1604B can be a cam, such as in the form of a surface, slot, channel, or depression defined in the housing 1602. In some embodiments, the guide 1604B can include and/or define one or more of a straight path or section and a curved path or section. In some embodiments, the follower 1604A can be a cam follower such as in the form of a roller, bearing, or the like, shaped and designed to move along and follow a path (e.g., slot, channel, depression) defined by the guide 1604B. The follower 1604A, when moving along the guide 1604B, is confined to motion limited by the path defined by guide 1604B. Stated differently, a cam (e.g., guide 1604B) and cam follower (e.g., follower 1604A) can be used to provide a combination of linear movement and lateral movement of a cutting element 1610.

Figure 16A:
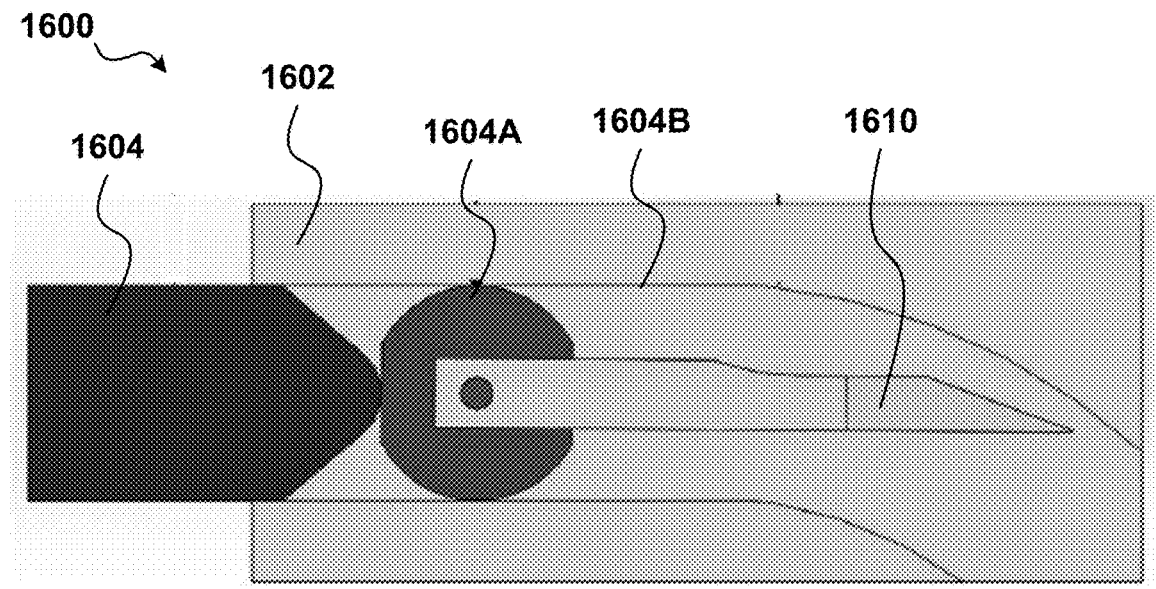
FIGS. 16A-16D depict side views of a cutting device in different configurations, according to an embodiment.
Figure 16B:
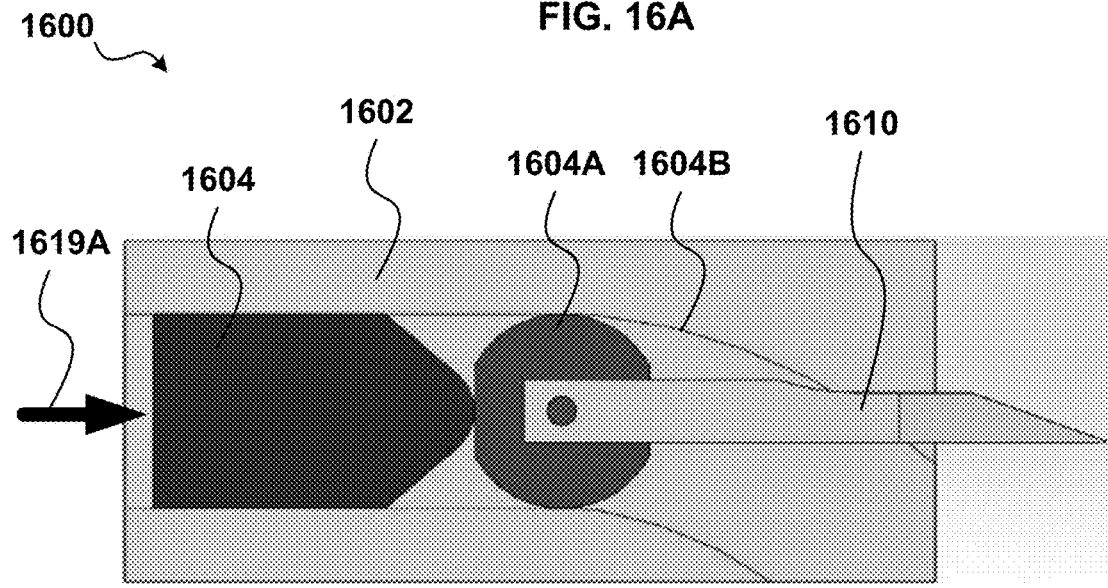
Figure 16C:
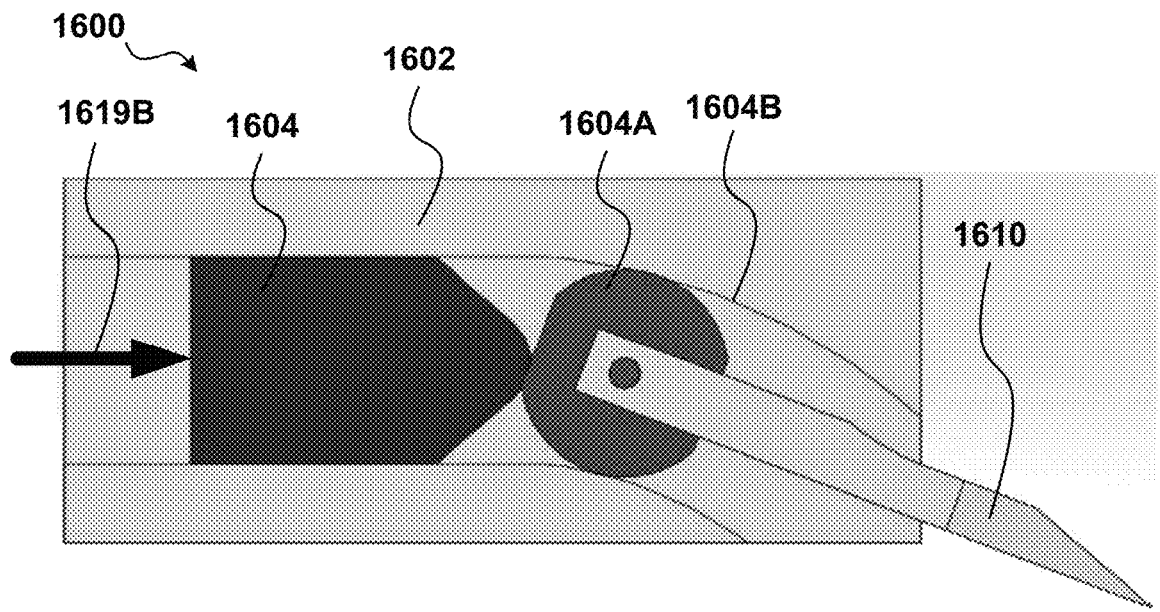

As depicted in FIG. 16B, movement 1619A of the actuator of the actuation assembly 1604 can be transferred and applied to the follower 1604A, to which the cutting element 1610 is attached. The movement 1619A can be a linear movement or motion corresponding to the motion of the actuator. As depicted in FIG. 16C, continued movement 1619B of the actuator can be transferred and applied to the follower 1604A. The continued movement 1619B can be a linear movement or motion corresponding to the motion of the actuator. The guide 1604B in conjunction with the follower 1604A can transform the linear motion of the actuator into a combination of linear and lateral motion of the cutting element 1610.

Figure 16D:
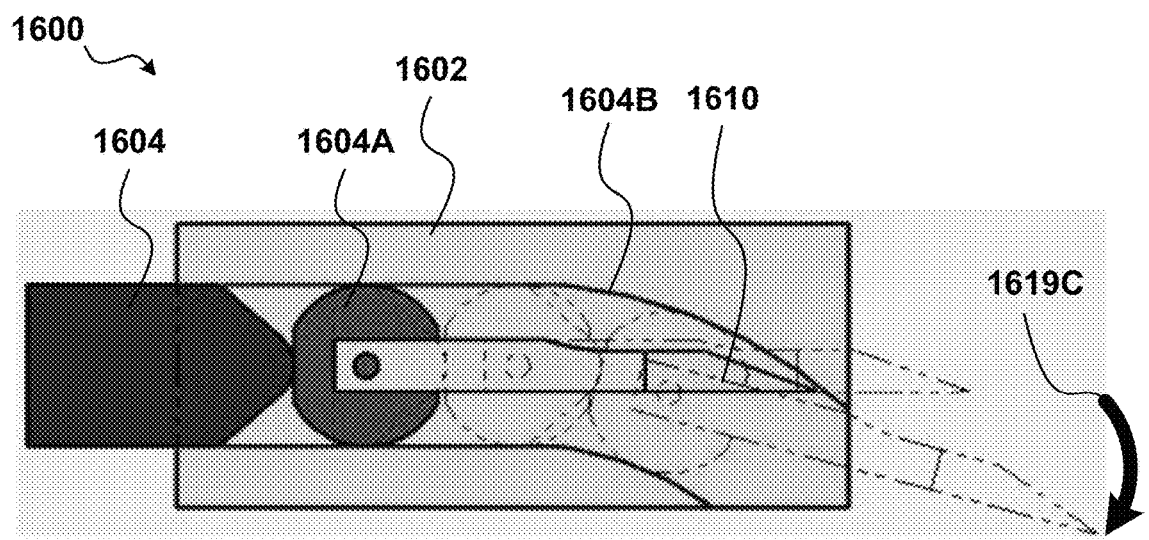

As depicted in FIG. 16D, the movement 1619A of the actuator is transferred and applied to the follower 1604A to cause a motion of the cutting element 1610. The continued movement 1619B of the movable component is similarly transferred and applied to the follower 1604A such that, upon traversal of and movement past a predetermined point (e.g., coinciding with a transition from a straight section to a curved section of the guide 1604B), the follower 1604A along with the cutting element 1610 are subjected to lateral motion 1619C. FIG. 16D depicts an example motion of the follower 1604A and the cutting element 1610. The lateral motion 1619C can include, for example, a hacking or swinging motion.

More specifically, movements 1619A and 1619B of the actuator (of the actuation assembly 1604) cause movement of the follower 1604A along the guide 1604B, such that the movement along a curved section of the guide 1604B causes the lateral motion 1619C of the cutting element 1610. While the follower 1604A is in the straight section of the guide 1604B, the follower 1604A and cutting element 1610 can move (e.g., slide) in a straight path. When the follower reaches the curved section of the guide 1604B, the follower 1604A and cutting element 1610 can begin to move laterally or radially as the follower 1604A continues to move along the guide 1604B. As shown in FIGS. 16A-16D, to cause the motion of the follower 1604A, including both the straight and curved movement, the actuator can move in a straight path.

FIGS. 18-23 depict an example cutting device 1800. The cutting device 1800 can include components that are structurally and/or functionally similar to other cutting devices described herein, e.g., cutting device 100, 200, and 500. For example, the cutting device 1800 can include a housing 1802, an actuation mechanism 1804, a cutting element 1810, a coupling mechanism 1806, and a depth control element implemented as a tissue contact surface 1801. While not depicted, cutting device 1800 can be used with a positioning element but can also be used alone.

Figure 20:
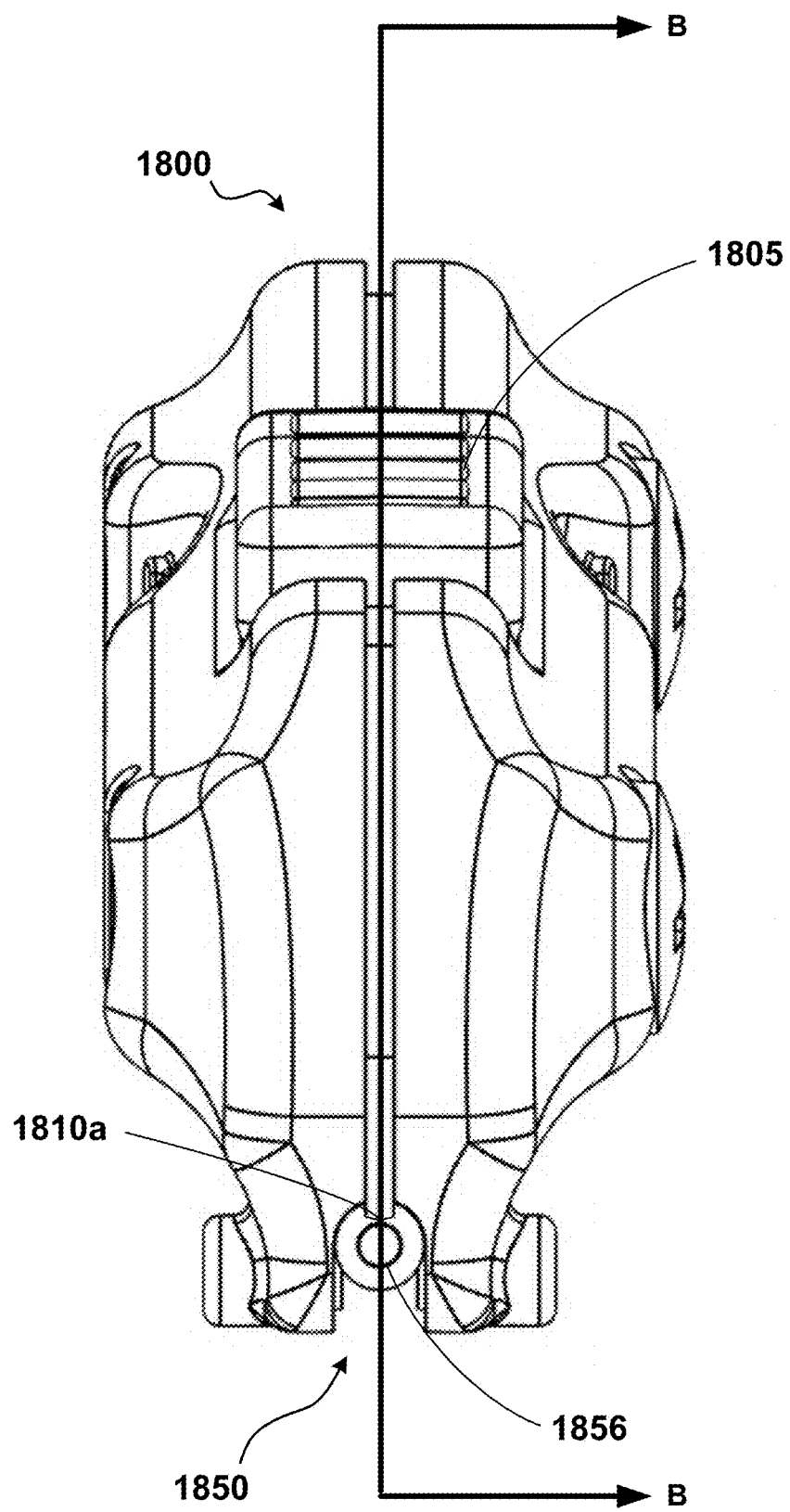
FIG. 20 depicts a view of a distal end of the cutting device shown in FIG. 18, according to embodiments.
Figure 21:
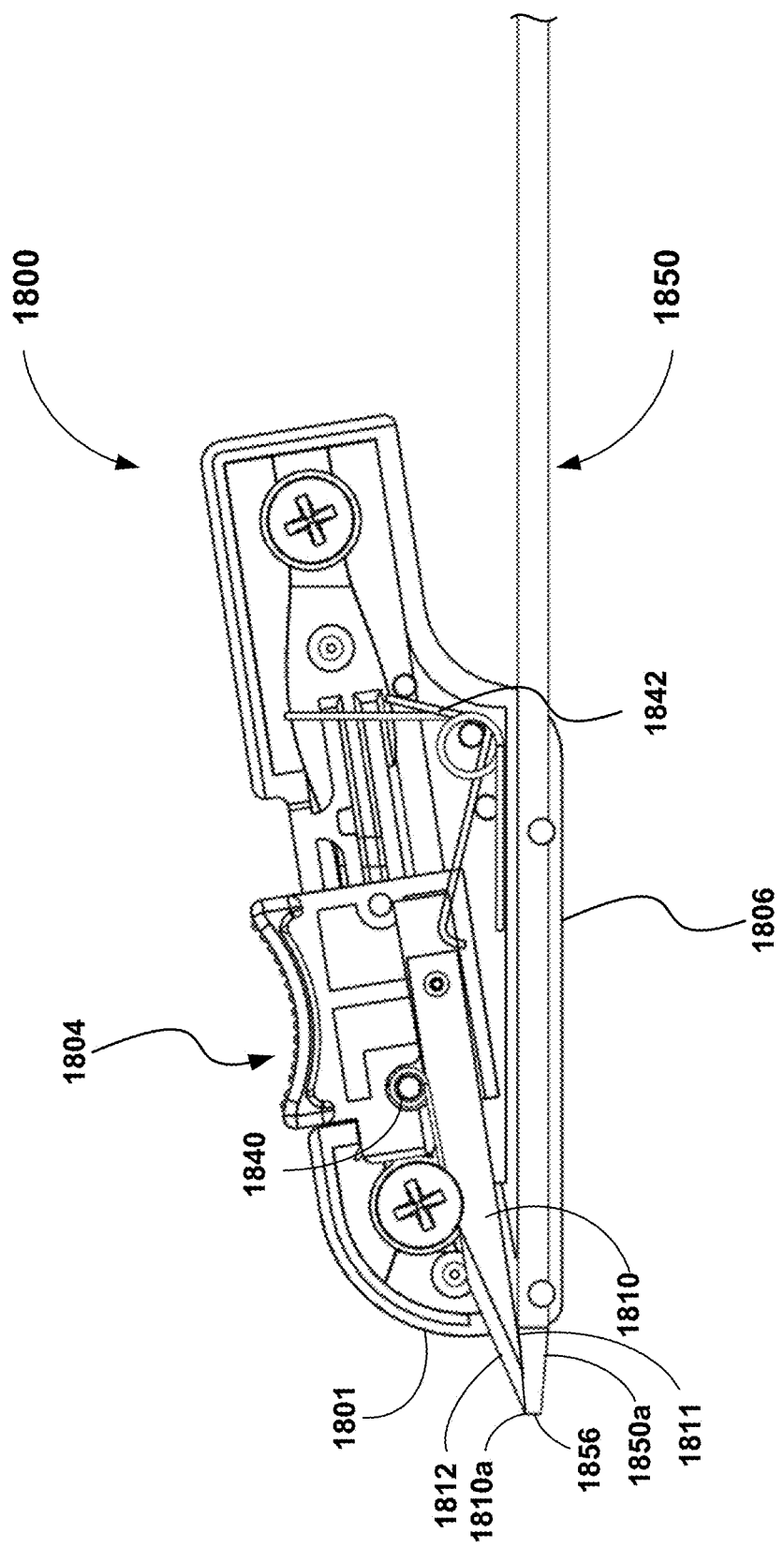
FIGS. 21 and 22 depict a cross-sectional view of the cutting device shown in FIG. 18, taken along B-B as shown in FIG. 20, according to embodiments.
Figure 22:
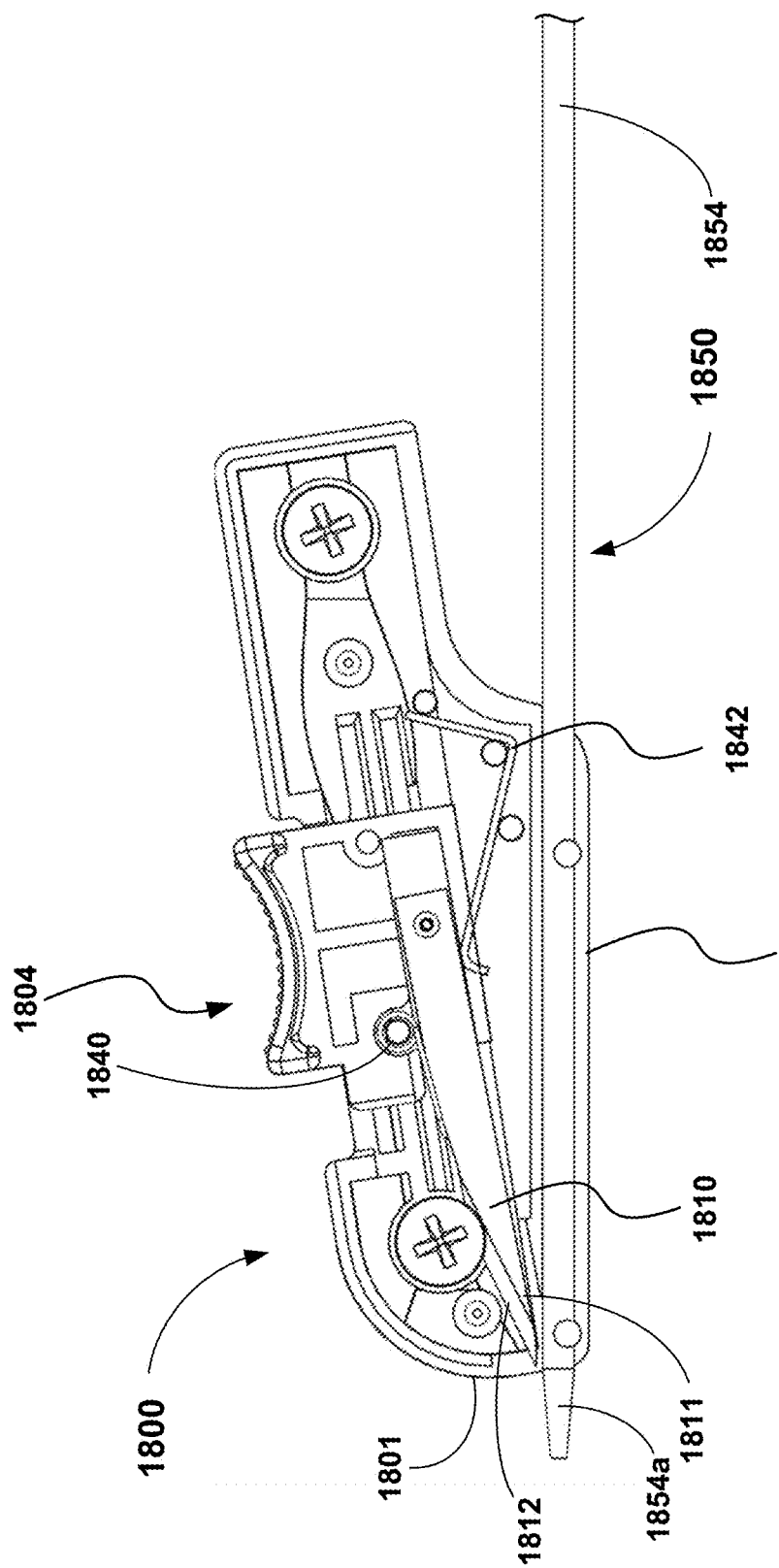

The cutting device 1800 is reversibly coupleable to a medical device, e.g., a dilator 1850 as shown in FIGS. 20-22, via the coupling mechanism 1806. The coupling mechanism 1806 includes two fastening or coupling points 1806a, 1806b. At each coupling point 1806a, 1806b, one or more plugs or gripping mechanisms 1807a, 1807b (which can be rigid or flexible) can be used to reversibly couple to the dilator 1850. Alternatively or additionally, other types of coupling elements, e.g., clamps, clips, magnets, etc., can also be used to grip the dilator 1850. The coupling mechanism 1806 can be configured to couple to the dilator 1850 from a lateral direction, e.g., by moving the cutting device 1800 in a direction toward the longitudinal axis of the dilator 1850, and similarly to decouple from the dilator 1850 in a lateral direction. While not depicted in FIGS. 20-22, the dilator 1850 can include a proximal end including a hub (e.g., as described with reference to instrument 250 depicted in FIG. 2). Accordingly, the cutting device 1800, by being laterally coupleable and decoupleable from the dilator 1850, is capable of being separated from the dilator 1850 even while the dilator 1850 is disposed over a guidewire that is disposed within a patient. Once coupled to the dilator 1850, the coupling mechanism 1806 can generate sufficient friction against the dilator 1850 to prevent movement (e.g., sliding and/or rotation) of the cutting device 1800 relative to the dilator 1850. The coupling mechanism 1806 includes more than one coupling point (i.e., two coupling points 1806a, 1806b) such that the coupling points collectively prevent pivoting and/or displacement of the cutting device 1800 relative to the dilator 1850. The dilator 1850 itself may have a degree of flexibility, and therefore having multiple points of coupling can ensure that the dilator 1850 remains aligned with the cutting device 1800 during use.

In the embodiment depicted, the coupling point 1806a can be located at or near a distal or front end of the cutting device 1806, to further ensure alignment between a cutting element 1810 of the cutting device and a longitudinal axis of the dilator (e.g., by reducing the risk of displacement between the end of the dilator 1850 and the cutting device 1800). Such alignment ensures that the cutting device 1800 does not form an incision that is offset from the puncture site, as depicted in FIG. 17A. In some embodiments, one or more components of the coupling mechanism 1806 can be controlled, e.g., via a mechanical or electrical actuator, to open and/or close to couple and decouple the cutting device 1800 to the dilator 1850. While two coupling points 1806a, 1806b are depicted in the figures, it can be appreciated that any number of coupling points or a continuous coupling point can be used to couple the cutting device 1800 to a medical instruction such as dilator 1850.

The housing 1802 can define a space of volume for receiving and housing a cutting element 1810 of the cutting device 1800. The housing 1802 can be ergonomically sized and shaped to enable a user (e.g., a physician) that is operating the device to hold the housing 1802 in a single handle and to actuate the actuation mechanism 1804 to deploy the cutting element 1810. In some embodiments, the housing 1802 can include certain ridges or indentations 1880, as well as other like features, to facilitate gripping by a user. The housing 1802 can support the actuation mechanism 1804 in a location where it can be easily manipulated by a finger of a user (e.g., an index finger or thumb of a user). In some embodiments, the housing 1802 can support the actuation mechanism 1804 along a side of the cutting device 1800 that faces away from the dilator 1850 when the two are coupled together. For example, the housing 1802 can support the actuation mechanism 1800 on a side of the cutting device 1800 that is opposite from the side including the coupling mechanism 1806 or on a side of the cutting device 1800 furthest away from the dilator 1850 in a direction radial to the longitudinal axis of the dilator 1850. The actuation mechanism 1804, as disposed, can be capable of being operated by both left and right handed users. In alternative embodiments, the actuation mechanism 1804 can be supported by the housing in other locations along its surface, e.g., such as the actuation mechanism 504 of the cutting device 500.

Figure 23:
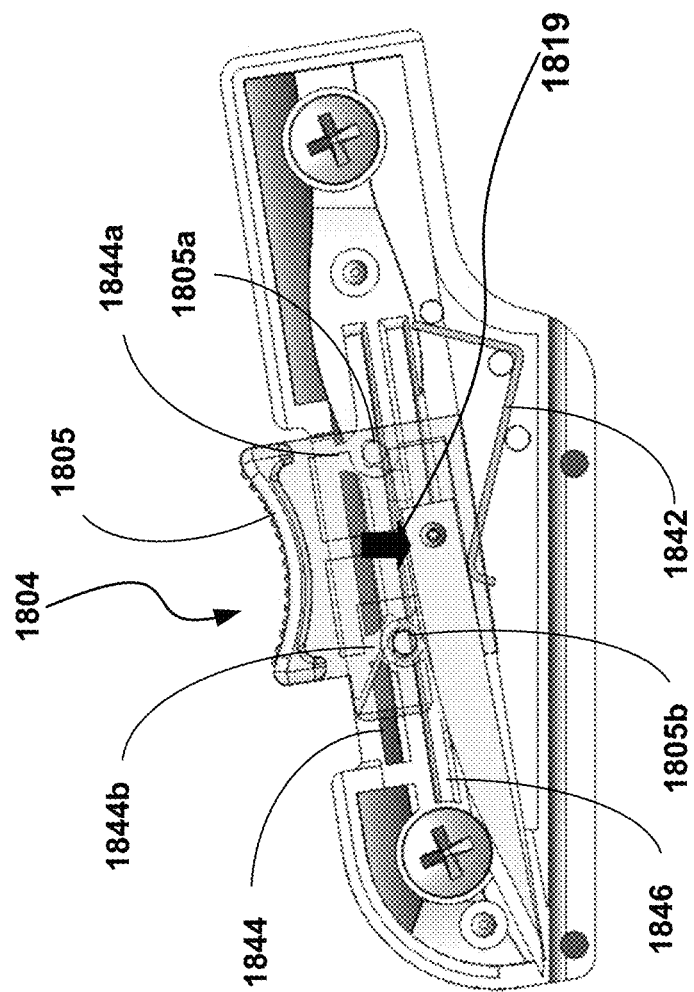
FIG. 23 depicts another cross-sectional view of the cutting device shown in FIG. 18, with certain components depicted transparently to show a locking mechanism of the device, according to embodiments.

The cutting element 1810 is moveable between a first position, i.e., a fully retracted or undeployed position, and a second position, i.e., a fully extended or deployed position. Cross-sectional views of the retracted position are depicted in FIGS. 22 and 23, and views of the extended position are depicted in FIGS. 18, 20, and 21. In the retracted position, the cutting element 1810 can be disposed entirely within the housing 1802, e.g., such that any cutting surfaces or edges of the cutting element 1810 are shielded within the housing 1802. In the extended position, the cutting element 1810 can extend out from a distal surface 1801 of the cutting device 1800. The cutting element 1810 can include an inner edge 1811 and an outer edge 1812. In some embodiments, both the inner and outer edges 1811, 1812 can be cutting edges, e.g., designed to cut tissue. In some embodiments, the outer edge 1812 can be a cutting edge while the inner edge 1811 can be a non-cutting edge. In some embodiments, one or both of the inner and outer edges 1811, 1812 can include a non-cutting portion and a cutting portion.

The cutting element 1810, in the fully extended position, can have a portion of its inner edge 1811 extend along or substantially along a distal end 1850a of the dilator 1850 in contact with an outer surface of the distal end 1850a, as depicted in FIG. 21. Similar to that described above with reference to cutting element 510 of cutting device 500, the cutting element 1810 can be angled such that its inner edge 1811 extends along the outer surface of the distal end 1850a of the dilator 1850. In the fully extended position, the distal end 1810a of the cutting element 1810 terminates at (or substantially near) the distal end of the dilator 1850. In some embodiments, the cutting device 1800 can include a spring 1840 (e.g., a torsion spring, an elastic spring, etc.) that applies a force upon the cutting element 1810 that pushes the cutting element 1810 against an outer surface of the dilator 1850. The force applied by the spring 1840 can further ensure that the inner edge 1811 of the cutting element 1810 is disposed against the outer surface of the dilator 1850. The dilator 1850 includes a lumen 1856 for receiving a guidewire, e.g., such as a guidewire being used in a Seldinger procedure. When used in a Seldinger procedure, the dilator 1850 can be slid down a length of the guidewire to a puncture site, and the cutting element 1810 can be extended to form an incision. The cutting element 1810, by being disposed against an outer surface of the dilator 1850 and with its distal end 1810a extending to the distal end of the dilator 1850, ensures that the incision formed by the cutting element 1810 extends from the puncture site.

The size of the incision formed by the cutting element 1810 can be sized to a particular medical instrument, e.g., the dilator 1850. The size of the incision can be controlled by a length that the cutting element 1810 extends and an angle at which the outer cutting edge is angled relative to the longitudinal axis of the dilator 1850, as described in more detail above with respect to cutting element 510 of cutting device 500. The cutting device 1800 can include a depth control element implemented as a tissue contacting surface 1801. The surface 1801 can be configured to contact the tissue surface near the puncture site to prevent further insertion of the cutting element 1800 into the tissue. Therefore, in use, the cutting device 1800 mounted on the dilator 1850 can be slid down a length of the guidewire until the distal surface 1801 contacts the tissue surface and prevents further insertion of the cutting element 1810 into the tissue. The cutting element 1810 can be extended prior to, during, or after sliding the cutting device 1800 with the dilator 1850 down along the length of the guidewire to form the incision.

The actuation mechanism 1804 can be used to extend and retract the cutting element 1810. In some embodiments, the cutting device 1800 can include a locking mechanism that locks or prevents movement of the actuation mechanism 1804 until the actuation mechanism is depressed. The locking mechanism can prevent unintentional movement of the actuation mechanism 184 and therefore unintentional movement of the cutting element 1810. In some embodiments, the locking mechanism can include a track or guide 1846, a spring 1842 (e.g., a torsion spring, elastic spring, etc.), and a plate or other structural component 1844 that defines one or more openings 1844a, 1844b. The actuation mechanism 1804 can include one or more protrusions or detents 1805a, 1805b. The spring 1842 can be configured to apply a force against the actuation mechanism 1804 that positions the detents 1805a, 1805b of the actuation mechanism 1804 within the openings 1844a, 1844b of the plate 1844. The actuation mechanism 1804 with the detents 1805a, 1805b so positioned is prevented from moving, e.g., by detents 1805a, 1805b coming into contact with opposing surfaces of the plate 1844.

In use, the actuation mechanism 1804 can be depressed into the housing 1802 (as shown by arrow 1819) such that the detents 1805a, 1805b move through the openings 1844a, 1844b and into the track 1846. For example, a user can apply sufficient force to overcome the force applied by the spring 1842 to depress the actuation mechanism 1804. The actuation mechanism 1804 can then be pushed forward (i.e., toward a distal surface 1801 of the cutting device 1800) with the detents 1805a, 1805b travelling along the track 1846, thereby extending the cutting element 1810. The actuation mechanism 1804, without first being depressed downward into the housing 1802, is prevented from moving such that accidental taps against the actuation mechanism 1804 do not cause unintentional extension of the cutting element 1810.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; and that embodiments may be practiced otherwise than as specifically described and claimed without departing from the scope and spirit of the present disclosure. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope and spirit of the present disclosure.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. For example, in some instances, "approximately a diameter of an instrument" may mean within ±10% of the length of the instrument. The terms "about" and "approximately" may be used interchangeably.

Also, various concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. A kit, comprising:
   a dilator including a proximal hub and an elongate body, the dilator disposable about a wire that has been inserted into a puncture site formed in tissue; and
   a cutting device reversibly coupleable to the dilator, the cutting device including:
     a housing;
     a set of couplers configured to (1) couple to the elongate body of the dilator and (2) decouple from the elongate body of the dilator when the dilator is disposed about the wire and the cutting device is moved laterally away from a longitudinal axis of the dilator; and
     a cutting element movable between (1) a fully retracted position in which the cutting element is disposed within the housing and (2) a fully extended position in which a distal end of the cutting element extends distally from the housing and is configured to form an incision in the tissue that extends from the puncture site, the cutting element configured to be disposed radially outward from a lumen of the dilator in the fully retracted and fully extended positions,
     the cutting element including (1) an inner edge having a portion that extends along a tapered distal portion of the dilator in contact with an outer surface of the dilator and (2) a distal end that terminates at a distal end of the dilator, when the cutting element is in the fully extended position and the cutting device is coupled to the dilator.

2. The kit of claim 1, wherein the set of couplers is configured to couple to the elongate body having a diameter of about 1 mm to about 4 mm.

3. The kit of claim 1, wherein the cutting device further includes a sliding actuator supported on the housing, the sliding actuator configured to move the cutting element into the fully extended position when the cutting device is coupled to the dilator and the dilator is disposed about the wire such that the cutting element can form the incision.

4. The kit of claim 3, wherein the set of couplers and the sliding actuator are supported on opposite sides of the housing.

5. The kit of claim 3, wherein:
the cutting device further includes a spring configured to apply a force on the sliding actuator to place the sliding actuator in a locked position,
the sliding actuator includes a set of detents configured to engage a set of locking surfaces within the housing when the sliding actuator is in the locked position to prevent movement of the sliding actuator,
the sliding actuator is movable from the locked position to an unlocked position in response to being moved toward the housing,
the sliding actuator is configured to slide along a track within the housing when the sliding actuator is in the unlocked position to move the cutting element from the fully retracted position to the fully extended position.

6. The kit of claim 1, further comprising a catheter configured to be placed through the incision into a target vessel,
wherein the housing includes a distal surface configured to limit a depth of insertion of the cutting element into the tissue such that the incision has a length that is approximately equal to a diameter of the catheter.

7. The kit of claim 1, wherein the dilator is included in a progressive set of dilators, the kit further comprising:
a catheter configured to be placed through the incision into a target vessel; and
the progressive set of dilators, each dilator from the progressive set of dilators disposable about the wire to dilate the incision, the progressive set of dilators increasing in size from a diameter of the dilator to a diameter of the catheter.

8. The kit of claim 1, wherein the cutting device further includes a spring configured to apply a force on the cutting element such that the cutting element is pressed against the outer surface of the tapered distal portion of the dilator.

9. The kit of claim 1, wherein the set of couplers includes a first coupler disposed at or near a distal end of the cutting device and a second coupler disposed at or near a proximal end of the cutting device.

10. The kit of claim 1, wherein the cutting element further includes an outer edge, the outer and inner edges of the cutting element extending toward the longitudinal axis of the dilator when the cutting device is coupled to the dilator.

11. The kit of claim 1, wherein the set of couplers is a first set of couplers, the kit further comprising:
a spacer configured to prevent proximal movement of the housing relative to the dilator, the spacer including a second set of couplers configured to reversibly couple the spacer to the dilator, the spacer sized to extend longitudinally along the dilator from a distal end of the proximal hub of the dilator to a most proximal coupler from the first set of couplers when the spacer and the cutting device are coupled to the dilator.

12. A kit, comprising:
a dilator including a proximal hub and a tapered distal portion, the dilator disposable about a wire that has been inserted into a puncture site formed in tissue; and
a cutting device reversibly coupleable to the dilator, the cutting device including:
a housing;
a set of couplers configured to reversibly couple the cutting device to the dilator;
a cutting element including an inner edge and an outer edge, the cutting element movable between a fully retracted position and a fully extended position,
the cutting element in the fully retracted position being disposed within the housing,
the cutting element in the fully extended position having a distal end that extends distally from the housing with (1) the inner edge extendable along the tapered distal portion of the dilator to a tip of the dilator and (2) the outer edge configured to form an incision in the tissue that extends from the puncture site, the outer and inner edges of the cutting element extending toward a longitudinal axis of the dilator when the cutting device is coupled to the dilator,
the cutting element configured to be disposed radially outward from a lumen of the dilator in the fully retracted and fully extended positions; and
a sliding actuator supported by the housing, the sliding actuator configured to move the cutting element into the fully extended position when the cutting device is coupled to the dilator and the dilator is disposed about the wire such that the cutting element can form the incision.

13. The kit of claim 12, wherein the set of couplers and the sliding actuator are supported on opposite sides of the housing.

14. The kit of claim 12, wherein:
the cutting device further includes a spring configured to apply a force on the sliding actuator to place the sliding actuator in a locked position,
the sliding actuator includes a set of detents configured to engage a set of locking surfaces within the housing when the sliding actuator is in the locked position to prevent movement of the sliding actuator,
the sliding actuator is movable from the locked position to an unlocked position in response to being moved toward the housing,
the sliding actuator is configured to slide along a track within the housing when the sliding actuator is in the unlocked position to move the cutting element from the fully retracted position to the fully extended position.

15. The kit of claim 12, further comprising a catheter configured to be placed through the incision into a target vessel,
wherein the housing includes a distal surface configured to limit a depth of insertion of the cutting element into the tissue such that the incision has a length that is approximately equal to a diameter of the catheter.

16. The kit of claim 12, wherein the dilator is included in a progressive set of dilators, the kit further comprising:
a catheter configured to be placed through the incision into a target vessel; and
the progressive set of dilators, each dilator from the progressive set of dilators disposable about the wire to dilate the incision, the progressive set of dilators increasing in size from a diameter of the dilator to a diameter of the catheter.

17. The kit of claim 12, wherein the cutting device further includes a spring configured to apply a force on the cutting element such that the cutting element is pressed against an outer surface of the tapered distal portion of the dilator.

18. The kit of claim 12, wherein the set of couplers includes a first coupler disposed at or near a distal end of the cutting device and a second coupler disposed at or near a proximal end of the cutting device.

19. The kit of claim 12, wherein the set of couplers is configured to decouple from the dilator when the dilator is disposed about the wire and the cutting device is moved in a direction lateral to the longitudinal axis of the dilator.

20. A kit, comprising:
a dilator including a proximal hub, an elongate body, and a tapered distal portion, the dilator disposable about a wire that has been inserted into a puncture site formed in tissue; and
a cutting device reversibly coupleable to the dilator, the cutting device including:
a housing;
a set of couplers configured to (1) couple to the elongate body of the dilator and (2) decouple from the elongate body of the dilator when the dilator is disposed about the wire and the cutting device is moved laterally away from a longitudinal axis of the dilator;
a cutting element movable between (1) a fully retracted position in which the cutting element is disposed within the housing and (2) a fully extended position in which a distal end of the cutting element extends distally from the housing and is configured to form an incision in the tissue that extends from the puncture site, the cutting element configured to be disposed radially outward from a lumen of the dilator in the fully retracted and fully extended positions; and
a spring configured to apply a force on the cutting element such that the cutting element is pressed against an outer surface of the tapered distal portion of the dilator when the cutting device is coupled to the dilator and the cutting element is in the fully extended position.

21. The kit of claim 20, wherein the cutting device further includes a sliding actuator supported by the housing, the sliding actuator configured to move the cutting element into the fully extended position when the cutting device is coupled to the dilator and the dilator is disposed about the wire such that the cutting element can form the incision.

22. The kit of claim 20, wherein the set of couplers includes a first coupler disposed at or near a distal end of the cutting device and a second coupler disposed at or near a proximal end of the cutting device.

23. The kit of claim 20, wherein the cutting element includes outer and inner edges that extend toward the longitudinal axis of the dilator when the cutting device is coupled to the dilator.

24. The kit of claim 20, further comprising a catheter configured to be placed through the incision into a target vessel,
wherein the housing includes a distal surface configured to limit a depth of insertion of the cutting element into the tissue such that the incision has a length that is approximately equal to a diameter of the catheter.

25. The kit of claim 20, wherein the dilator is included in a progressive set of dilators, the kit further comprising:
a catheter configured to be placed through the incision into a target vessel; and
the progressive set of dilators, each dilator from the progressive set of dilators disposable about the wire to dilate the incision, the progressive set of dilators increasing in size from a diameter of the dilator to a diameter of the catheter.

26. A kit, comprising:
a dilator including a proximal hub and an elongate body, the dilator disposable about a wire that has been inserted into a puncture site formed in tissue; and
a cutting device reversibly coupleable to the dilator, the cutting device including:
a housing;
a set of couplers configured to (1) couple to the elongate body of the dilator and (2) decouple from the elongate body of the dilator when the dilator is disposed about the wire and the cutting device is moved laterally away from a longitudinal axis of the dilator; and
a cutting element movable between (1) a fully retracted position in which the cutting element is disposed within the housing and (2) a fully extended position in which a distal end of the cutting element extends distally from the housing and is configured to form an incision in the tissue that extends from the puncture site, the cutting element configured to be disposed radially outward from a lumen of the dilator in the fully retracted and fully extended positions, the cutting element including outer and inner edges that extend toward the longitudinal axis of the dilator when the cutting device is coupled to the dilator.

27. The kit of claim 26, wherein the cutting device further includes a sliding actuator supported by the housing, the sliding actuator configured to move the cutting element into the extended position when the cutting device is coupled to the dilator and the dilator is disposed about the wire such that the cutting element can form the incision.

28. The kit of claim 26, wherein the set of couplers includes a first coupler disposed at or near a distal end of the cutting device and a second coupler disposed at or near a proximal end of the cutting device.

29. The kit of claim 26, further comprising a catheter configured to be placed through the incision into a target vessel,
wherein the housing includes a distal surface configured to limit a depth of insertion of the cutting element into the tissue such that the incision has a length that is approximately equal to a diameter of the catheter.

30. The kit of claim 26, wherein the dilator is included in a progressive set of dilators, the kit further comprising:
a catheter configured to be placed through the incision into a target vessel; and
the progressive set of dilators, each dilator from the progressive set of dilators disposable about the wire to dilate the incision, the progressive set of dilators increasing in size from a diameter of the dilator to a diameter of the catheter.

\* \* \* \* \*